United States Patent
Schwab et al.

(10) Patent No.: US 12,203,118 B2
(45) Date of Patent: Jan. 21, 2025

(54) NORCOCLAURINE SYNTHASES WITH INCREASED ACTIVITY

(71) Applicant: RIVER STONE BIOTECH, INC., Wilmington, DE (US)

(72) Inventors: Markus Schwab, Reinach (CH); Franziska Grassinger, Reinach (CH); Laura Occhipinti, Reinach (CH); Philipp Friedrich Berninger, Reinach (CH); Jon Richard Heal, Reinach (CH); Joseph Michael Sheridan, Reinach (CH); Anaelle Hatsch, Reinach (CH); Jens Houghton-Larsen, Copenhagen (DK)

(73) Assignee: RIVER STONE BIOTECH, INC., Wilmington, DE (US)

( * ) Notice: Subject to any disclaimer, the term of this patent is extended or adjusted under 35 U.S.C. 154(b) by 1378 days.

(21) Appl. No.: 16/623,053

(22) PCT Filed: Jun. 18, 2018

(86) PCT No.: PCT/EP2018/066153
§ 371 (c)(1),
(2) Date: Dec. 16, 2019

(87) PCT Pub. No.: WO2018/229305
PCT Pub. Date: Dec. 20, 2018

(65) Prior Publication Data
US 2023/0193333 A1    Jun. 22, 2023

(30) Foreign Application Priority Data

Jun. 16, 2017  (DK) .............................. PA201770474
Jun. 30, 2017  (DK) .............................. PA201770533

(51) Int. Cl.
| | | |
|---|---|---|
| C12P 17/16 | (2006.01) | |
| C12N 1/21 | (2006.01) | |
| C12N 9/88 | (2006.01) | |
| C12N 15/60 | (2006.01) | |

(52) U.S. Cl.
CPC .............. *C12P 17/165* (2013.01); *C12N 9/88* (2013.01); *C12Y 402/01078* (2013.01)

(58) Field of Classification Search
None
See application file for complete search history.

(56) References Cited

U.S. PATENT DOCUMENTS

| | | | | |
|---|---|---|---|---|
| 10,119,155 B2 * | 11/2018 | Facchini | ................. | C12P 17/12 |
| 2006/0014264 A1 | 1/2006 | Sauer | | |

FOREIGN PATENT DOCUMENTS

| | | | |
|---|---|---|---|
| WO | WO 2014/143744 A2 | 9/2014 | |
| WO | WO 2015/066642 | 5/2015 | |
| WO | WO2015/164960 A1 | 11/2015 | |
| WO | WO-2015192233 A1 * | 12/2015 | ........... C12N 9/0022 |
| WO | WO 2016/049364 | 3/2016 | |
| WO | WO 2017/122189 | 7/2017 | |
| WO | WO 2018/075670 A1 | 4/2018 | |
| WO | WO 2018/229305 | 12/2018 | |
| WO | WO 2020/078837 A1 | 4/2020 | |
| WO | WO 2020/144371 A1 | 7/2020 | |

OTHER PUBLICATIONS

Uniprot, Accession No. Q67A25, 2016, www.uniprot.org. (Year: 2016).*
Lichman, Enzyme catalysed Pictet-Spengler formation of chiral 1,1'-disubstituted- and spiro-tetrahydroisoquinolines, Nature Comm. 8, 2017, 14883. (Year: 2017).*
Pesnot et al., The Catalytic Potential of Coptis japonica NCS2 Revealed, Adv. Synth Catal. 354, 2012, 2997-3008. (Year: 2012).*
GenBank, Accession No. A2A1A1.2, 2016, www.ncbi.nlm.nih.gov (Year: 2016).*
GenBank, Accession No. EU883006.1, 2009, ncbi.nlm.nih.gov (Year: 2009).*
Genbank, Accession No. AB267399, 2010, www.ncbi.nlm.gov. (Year: 2010).*
Grewal et al., Peroxisome compartmentalization of a toxic enzyme improves alkaloid production, Nature Chem. Biol. 17, 2021, 96-103. (Year: 2021).*
Trenchard et al., De novo production of the key branch point benzylisoquinoline alkaloid reticuline in yeast, Metabolic Eng. 31, 2015 , 74-83. (Year: 2015).*
GenBank, Accession No. AAR22502, 2004, www.ncbi.nlm.nih.gov. (Year: 2004).*
Pesnot et al., The Catalytic Potential of Coptis japonica NCS2 Revealed—Development and Utilisation of a Fluorescamine-Based Assay, Adv. Synth. Catal. 354, 2012, 2997-300. (Year: 2012).*
Bateman A, et al. Pfam 3.1: 1313 multiple alignments and profile HMMs match the majority of proteins. Nucl. Acids Res., 27(1): 260-62 (1999).

(Continued)

*Primary Examiner* — Todd M Epstein
(74) *Attorney, Agent, or Firm* — McDonnell Boehnen Hulbert & Berghoff LLP

(57) ABSTRACT

The invention relates to norcoclaurine synthases and substrate binding sites having one or more site-specific mutation which increase the activity, when compared to the wild type synthase, of the condensation of 4-HPAA and dopamine to (S)-norcoclaurine and/or 3,4-DhPAA and dopamine to (S)-norlaudanosoline. The inventors both identified specific mutations corresponding to at position 73, 75, 77, 82, 99, 114, 141, 142, 147, 152, 174 and/or 178 in the count according to SEQ ID No: 1, and sites corresponding to the binding domains defined in SEQ ID NO: 4 and 5, where the mutated increase of the activity may be positioned within these norcoclaurine synthases. These domains are conserved regions.

18 Claims, 8 Drawing Sheets
Specification includes a Sequence Listing.

(56) References Cited

OTHER PUBLICATIONS

Bonamore A., et al. Norcoclaurine Synthase: Mechanism of an Enantioselective Pictet-Spenger Catalyzing Enzyme. Molecules 15, 2070-78 (2010).
Deloache W.C., et al. An enzyme-coupled biosensor enables (S)-reticuline production in yeast from glucose. Nat. Chem. Biol. 11, 465-71 (2015).
Galanie S, et al. Complete biosynthesis of opioids in yeast. Science, 349(6252): 1095-1100 (2015).
Geitz R.D. and R.H. Schiestl. High-efficiency yeast transformation using the LiAc/SS carrier DNA/PEG method. Nat. Protoc. 2, 31-34 (2007).
Giaever G and C Nislow The Yeast Deletion Collection: A Decade of Functional Genomics. Genetics, vol. 197, 451-65 (2014).
Ilari A, et al. Structural Basis of Enzymatic (S)-Norcoclaurine Biosynthesis. J Biol. Chem. vol. 284, No. 2, pp. 897-904 (2009).
Lichman B.R., et al. 'Dopamine-first' mechanism enables the rational engineering of the norcoclaurine synthase aldehyde activity profile. FEBS Journal, 282, 1137-51 (2015).
Luttik, M.A.H., et al. Alleviation of feedback inhibition in Saccharomyces cerevisiae aromatic amino acid biosynthesis: Quantification of metabolic impact. Metabolic Engineering 10, 141-53 (2008).
Mumberg D, et al. Yeast vectors for the controlled expression of heterologous proteins in different genetic backgrounds. Gene, 156: 119-22 (1995).
Narcross L, et al. Microbial Factories for the Production of Benzylisoquinoline Alkaloids. Trends in Biotechnol. 34(3): 228-41 (2016).

Needleman, S.B. and C.D. Wunsch. A General Method Applicable to the Search for Similarities in the Amino Acid Sequence of Two Proteins. J. Mol. Biol. 48, 443-53 (1970).
Nicaud J-M. Yarowia lipolytica. Yeast 29: 409-18 (2012).
Prelich G. Gene Overexpression: Uses, Mechanisms and Interpretation. Genetics, vol. 190, 841-54 (2012).
Rice P., et al. EMBOSS: The European Molecular Biology Open Software Suite. TIG, vol. 16, No. 6 (2000).
Sonnhammer E.L.L., et al. Pfam: A Comprehensive Database of Protein Domain Families Based on Seed Alignments. Proteins: Structure, Function, and Genetics, 28:405-20 (1997).
Sonnhammer E.L.L., et al. Pfam: multiple sequence alignments and HMM-profiles of protein domains. Nucl. Acids Res. vol. 26, No. 1, 320-22 (1998).
Diamond et al., "Metabolic engineering for the production of plant isoquinoline alkaloids", Plant Biotechnology Journal, vol. 14(6):1319-1328 (Oct. 2015).
Polturak et al., "Elucidation of the first committed step in betalain biosynthesis enables the heterologous engineering of betalain pigments in plants", New Phytologist, vol. 210(1):269-283 (Dec. 2015).
Brohée, et al. (2010). "YTPdb: A wiki database of yeast membrane transporters." Biochim. Biophys. Acta Biomembr. 1798, 1908-1912.
Hawkins and Smolke (2008). "Production of benzylisoquinoline alkaloids in Saccharomyces cerevisiae." Nat. Chem. Biol. 4, 564-573.
Murphy and Lin (2001). "Vertebroplasty: a simple solution to a difficult problem." J. Clin. Densitom. 4, 189-197.
Schläger and Dräger (2016). "Exploiting plant alkaloids." Curr. Opin. Biotechnol. 37, 155-164.
Shitan, et al. (2014). "Alkaloid transporters in plants." Plant Biotechnol. (Tokyo) 31, 453-463.

* cited by examiner

SEQUENCE LISTING

<160> NUMBER OF SEQ ID NOS: 22

<210> SEQ ID NO 1
<211> LENGTH: 196
<212> TYPE: PRT
<213> ORGANISM: Coptis japonica

<400> SEQUENCE: 1

Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65                  70                  75                  80

Ile Thr Gly Asp Gly Gly Glu Gly Ser Ile Leu Asp Met Thr Phe Pro
                85                  90                  95

Pro Gly Gln Phe Pro His His Tyr Arg Glu Lys Phe Val Phe Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145                 150                 155                 160

Pro Glu Phe Ala Lys Ile Val Lys Pro Leu Ile Asp Thr Val Pro Leu
                165                 170                 175

Ala Ile Met Ser Glu Ala Ile Ala Lys Val Val Leu Glu Asn Lys His
            180                 185                 190

Lys Ser Ser Glu
        195

<210> SEQ ID NO 2
<211> LENGTH: 591
<212> TYPE: DNA
<213> ORGANISM: Coptis japonica

<400> SEQUENCE: 2
atgaggatgg aagttgttct agttgttttc ttgatgttca taggtacgat aaattgtgaa     60
agattgatat tcaatggacg accgctactc catcgcgtaa caaaagagga gactgtaatg    120
ctttatcatg agctggaagt agctgcttca gccgatgaag tgtggagtgt cgaaggttcg    180
cctgagttgg gcttgcattt gcctgacttg ctccctgctg gtatatttgc aaagtttgaa    240
attactggtg atggaggtga aggttcgatc ctggacatga cattcccccc aggtcagttt    300
ccacatcatt acagggagaa gttcgtgttc ttcgatcaca gaatcgttta caagttagta    360
gaacagatcg atggtgattt tttcgatcta ggtgttacat actatatgga tacaatccga    420
gttgttgcga caggccctga ttcatgtgtc atcaagtcta ctactgaata ccatgtgaaa    480
cctgagtttg ccaaaatcgt caaaccactt attgacactg ttccactagc tatcatgtct    540
gaagcgattg caaaggttgt tctagagaac aaacacaaga gttcagagta a             591

<210> SEQ ID NO 3

```
<211> LENGTH: 591
<212> TYPE: DNA
<213> ORGANISM: Coptis japonica

<400> SEQUENCE: 3
atgagaatgg aagtcgtctt ggtcgttttc ttgatgttca ttggtactat caactgcgaa      60
agattgatct tcaatggtag acctttgttg cacagagtta ccaaagaaga aaccgttatg     120
ttgtaccacg aattggaagt tgctgcttct gctgatgaag tttggtctgt tgaaggttct     180
ccagaattgg gtttacattt gccagatttg ttgccagctg gtattttgc caagttcgaa      240 attactggtg atggtggtga aggttccatt ttggatatga cttttccacc aggtcaattc     300
ccacatcatt acagagaaaa gttcgtcttt ttcgaccaca gaacagata caagttggtc      360 gaacaaatcg atggtgattt cttcgatttg ggtgttactt actacatgga caccattaga     420
gttgttgcta ctggtccaga ttcttgcgtt attaagtcta ctactgaata ccacgtcaag     480
ccagaatttg ctaaaatcgt taagccattg atcgataccg ttccattggc tattatgtct     540
gaagctattg ccaaggttgt cttggaaaac aaacacaagt catctgaatg a              591

<210> SEQ ID NO 4
<211> LENGTH: 6
<212> TYPE: PRT
<213> ORGANISM: Coptis japonica

<400> SEQUENCE: 4

Pro Ala Gly Ile Phe Ala
1               5

<210> SEQ ID NO 5
<211> LENGTH: 11
<212> TYPE: PRT
<213> ORGANISM: Coptis japonica

<400> SEQUENCE: 5

Thr Val Pro Leu Ala Ile Met Ser Glu Ala Ile
1               5                   10

<210> SEQ ID NO 6
<211> LENGTH: 499
<212> TYPE: PRT
<213> ORGANISM: Beta vulgaris

<400> SEQUENCE: 6

Met Asp His Ala Thr Leu Ala Met Ile Leu Ala Ile Leu Phe Ile Ser
1               5                   10                  15

Phe His Phe Ile Lys Leu Leu Phe Ser Gln Gln Thr Thr Lys Leu Leu
                20                  25                  30

Pro Pro Gly Pro Lys Pro Leu Pro Ile Ile Gly Asn Ile Leu Glu Val
            35                  40                  45

Gly Lys Lys Pro His Arg Ser Phe Ala Asn Leu Ala Lys Ile His Gly
        50                  55                  60

Pro Leu Ile Ser Leu Arg Leu Gly Ser Val Thr Thr Ile Val Val Ser
65                  70                  75                  80

Ser Ala Asp Val Ala Lys Glu Met Phe Leu Lys Asp His Pro Leu
                85                  90                  95

Ser Asn Arg Thr Ile Pro Asn Ser Val Thr Ala Gly Asp His His Lys
            100                 105                 110

Leu Thr Met Ser Trp Leu Pro Val Ser Pro Lys Trp Arg Asn Phe Arg
        115                 120                 125
```

Lys Ile Thr Ala Val His Leu Leu Ser Pro Gln Arg Leu Asp Ala Cys
130                 135                 140

Gln Thr Phe Arg His Ala Lys Val Gln Gln Leu Tyr Glu Tyr Val Gln
145                 150                 155                 160

Glu Cys Ala Gln Lys Gly Gln Ala Val Asp Ile Gly Lys Ala Ala Phe
                165                 170                 175

Thr Thr Ser Leu Asn Leu Leu Ser Lys Leu Phe Phe Ser Val Glu Leu
            180                 185                 190

Ala His His Lys Ser His Thr Ser Gln Glu Phe Lys Glu Leu Ile Trp
        195                 200                 205

Asn Ile Met Glu Asp Ile Gly Lys Pro Asn Tyr Ala Asp Tyr Phe Pro
210                 215                 220

Ile Leu Gly Cys Val Asp Pro Ser Gly Ile Arg Arg Leu Ala Cys
225                 230                 235                 240

Ser Phe Asp Lys Leu Ile Ala Val Phe Gln Gly Ile Ile Cys Glu Arg
                245                 250                 255

Leu Ala Pro Asp Ser Ser Thr Thr Thr Thr Thr Thr Asp Asp Val
            260                 265                 270

Leu Asp Val Leu Leu Gln Leu Phe Lys Gln Asn Glu Leu Thr Met Gly
        275                 280                 285

Glu Ile Asn His Leu Leu Val Asp Ile Phe Asp Ala Gly Thr Asp Thr
290                 295                 300

Thr Ser Ser Thr Leu Glu Trp Val Met Thr Glu Leu Ile Arg Asn Pro
305                 310                 315                 320

Glu Met Met Glu Lys Ala Gln Glu Glu Ile Lys Gln Val Leu Gly Lys
                325                 330                 335

Asp Lys Gln Ile Gln Glu Ser Asp Ile Ile Asn Leu Pro Tyr Leu Gln
            340                 345                 350

Ala Ile Ile Lys Glu Thr Leu Arg Leu His Pro Pro Thr Val Phe Leu
        355                 360                 365

Leu Pro Arg Lys Ala Asp Thr Asp Val Glu Leu Tyr Gly Tyr Ile Val
370                 375                 380

Pro Lys Asp Ala Gln Ile Leu Val Asn Leu Trp Ala Ile Gly Arg Asp
385                 390                 395                 400

Pro Asn Ala Trp Gln Asn Ala Asp Ile Phe Ser Pro Glu Arg Phe Ile
                405                 410                 415

Gly Cys Glu Ile Asp Val Lys Gly Arg Asp Phe Gly Leu Leu Pro Phe
            420                 425                 430

Gly Ala Gly Arg Arg Ile Cys Pro Gly Met Asn Leu Ala Ile Arg Met
        435                 440                 445

Leu Thr Leu Met Leu Ala Thr Leu Leu Gln Phe Phe Asn Trp Lys Leu
450                 455                 460

Glu Gly Asp Ile Ser Pro Lys Asp Leu Asp Met Asp Glu Lys Phe Gly
465                 470                 475                 480

Ile Ala Leu Gln Lys Thr Lys Pro Leu Lys Leu Ile Pro Ile Pro Arg
                485                 490                 495

Tyr Gly Ser

<210> SEQ ID NO 7
<211> LENGTH: 1500
<212> TYPE: DNA
<213> ORGANISM: Beta vulgaris

<400> SEQUENCE: 7

```
atggatcatg ctaccttggc tatgattttg gccatcttgt tcattagctt ccacttcatc    60
aagctgttgt tctctcaaca aactaccaag ttgttgccac caggtccaaa accattgcca   120
attattggta acatcttgga ggttggtaag aagccacata gatcttttgc taatttggcc   180
aagattcacg gtccattgat ttctttgaga ttgggttctg ttacgaccat cgttgtttct   240
tcagctgatg ttgctaaaga gatgttcttg aagaaggatc acccattgtc aacagaact    300 attccaaatt ctgttaccgc tggtgatcat cataagttga ctatgtcttg gttgccagtt   360
tctccaaagt ggcgtaattt cagaaagatt accgctgttc atttgttgtc cccacaaaga   420
ttggatgctt gtcaaacttt tagacacgct aaggttcaac agttgtacga atacgttcaa   480
gaatgtgctc aaaaaggtca agccgttgat attggtaaag ctgcttttac tacctccttg   540
aacttgctgt ctaagttgtt cttctctgtt gaattggctc atcacaagtc tcatacctct   600
caagaattca agagctgat ctggaacatc atggaagata tcggtaagcc aaattacgct   660
gattacttcc aattttggg ttgcgttgat ccatctggta ttagaagaag attggcttgc   720
tctttcgata agttgattgc tgttttccaa ggtatcatct gtgaaagatt agccccagat   780
tcttctacta ctacaactac taccactgat gatgttttgg atgtgttgtt gcagttgttc   840
aagcaaaacg aattgaccat gggtgaaatc aaccacttgt tggttgatat tttcgatgct   900
ggtactgata ccacttcctc tactttggaa tgggttatga ccgaattgat cagaaaccca   960
gaaatgatgg aaaaggccca agaagagatt aagcaagttt tgggtaaaga caagcagatc  1020
caagaatccg atattatcaa cttgccatac ttgcaggcca tcatcaaaga acattgaga   1080 ttgcatccac caaccgtttt tttgttgcca agaaaagctg ataccgatgt tgagttgtat  1140
ggttacatcg ttccaaagga tgcccaaatc ttggttaatt tgtgggctat ggtagagat   1200 ccaaatgctt ggcaaaacgc cgatattttc tcaccagaaa ggttcattgg ttgcgaaatt  1260
gatgttaagg gtagagactt tggtttgttg ccttttggtg ctggtagaag gatttgtcca  1320
ggtatgaatt tggctatcag aatgttgact ttgatgctgg ctactctgtt gcaattttc   1380 aactggaaat tggagggtga catctccacca aaagatttgg atatggacga aaagttcggt  1440
atcgccttgc aaaaaactaa gccattgaag ttgatcccca ttcctagata cggttcttga  1500
```

<210> SEQ ID NO 8
<211> LENGTH: 470
<212> TYPE: PRT
<213> ORGANISM: Pseudomonas putida

<400> SEQUENCE: 8

```
Met Thr Pro Glu Gln Phe Arg Gln Tyr Gly His Gln Leu Ile Asp Leu
1               5                   10                  15

Ile Ala Asp Tyr Arg Gln Thr Val Gly Glu Arg Pro Val Met Ala Gln
                20                  25                  30

Val Glu Pro Gly Tyr Leu Lys Ala Ala Leu Pro Ala Thr Ala Pro Gln
            35                  40                  45

Gln Gly Glu Pro Phe Ala Ala Ile Leu Asp Asp Val Asn Asn Leu Val
        50                  55                  60

Met Pro Gly Leu Ser His Trp Gln His Pro Asp Phe Tyr Gly Tyr Phe
65                  70                  75                  80

Pro Ser Asn Gly Thr Leu Ser Ser Val Leu Gly Asp Phe Leu Ser Thr
                85                  90                  95

Gly Leu Gly Val Leu Gly Leu Ser Trp Gln Ser Ser Pro Ala Leu Ser
            100                 105                 110
```

Glu Leu Glu Glu Thr Thr Leu Asp Trp Leu Arg Gln Leu Leu Gly Leu
                115                 120                 125

Ser Gly Gln Trp Ser Gly Val Ile Gln Asp Thr Ala Ser Thr Ser Thr
130                 135                 140

Leu Val Ala Leu Ile Ser Ala Arg Glu Arg Ala Thr Asp Tyr Ala Leu
145                 150                 155                 160

Val Arg Gly Gly Leu Gln Ala Glu Pro Lys Pro Leu Ile Val Tyr Val
                165                 170                 175

Ser Ala His Ala His Ser Ser Val Asp Lys Ala Ala Leu Leu Ala Gly
                180                 185                 190

Phe Gly Arg Asp Asn Ile Arg Leu Ile Pro Thr Asp Glu Arg Tyr Ala
                195                 200                 205

Leu Arg Pro Glu Ala Leu Gln Ala Ala Ile Glu Gln Asp Leu Ala Ala
                210                 215                 220

Gly Asn Gln Pro Cys Ala Val Val Ala Thr Thr Gly Thr Thr Thr Thr
225                 230                 235                 240

Thr Ala Leu Asp Pro Leu Arg Pro Val Gly Glu Ile Ala Gln Ala Asn
                245                 250                 255

Gly Leu Trp Leu His Val Asp Ser Ala Met Ala Gly Ser Ala Met Ile
                260                 265                 270

Leu Pro Glu Cys Arg Trp Met Trp Asp Gly Ile Glu Leu Ala Asp Ser
                275                 280                 285

Val Val Val Asn Ala His Lys Trp Leu Gly Val Ala Phe Asp Cys Ser
290                 295                 300

Ile Tyr Tyr Val Arg Asp Pro Gln His Leu Ile Arg Val Met Ser Thr
305                 310                 315                 320

Asn Pro Ser Tyr Leu Gln Ser Ala Val Asp Gly Glu Val Lys Asn Leu
                325                 330                 335

Arg Asp Trp Gly Ile Pro Leu Gly Arg Arg Phe Arg Ala Leu Lys Leu
                340                 345                 350

Trp Phe Met Leu Arg Ser Glu Gly Val Asp Ala Leu Gln Ala Arg Leu
                355                 360                 365

Arg Arg Asp Leu Asp Asn Ala Gln Trp Leu Ala Gly Asn Val Glu Ala
                370                 375                 380

Ala Ala Glu Trp Glu Val Leu Ala Pro Val Gln Leu Gln Thr Leu Cys
385                 390                 395                 400

Ile Arg His Arg Pro Ala Gly Leu Glu Gly Glu Ala Leu Asp Ala His
                405                 410                 415

Thr Lys Gly Trp Ala Glu Arg Leu Asn Ala Ser Gly Ala Ala Tyr Val
                420                 425                 430

Thr Pro Ala Thr Leu Asp Gly Arg Trp Met Val Arg Val Ser Ile Gly
                435                 440                 445

Ala Leu Pro Thr Glu Arg Gly Asp Val Gln Arg Leu Trp Ala Arg Leu
450                 455                 460

Gln Asp Val Ile Lys Gly
465                 470

<210> SEQ ID NO 9
<211> LENGTH: 1413
<212> TYPE: DNA
<213> ORGANISM: Pseudomonas putida

<400> SEQUENCE: 9
atgaccccag aacaattcag acaatacggt caccaattga ttgatttgat cgccgattac    60

```
agacaaaccg ttggtgaaag accagttatg gctcaagttg aaccaggtta tttgaaagct    120
gctttgccag ctactgctcc acaacaaggt gaaccatttg ctgctatttt ggatgatgtt    180
aacaacttgg ttatgccagg tttgtctcat ggcaacatc cagatttta cggttacttt     240 ccatccaacg gtactttgtc atctgttttg ggtgatttct tgtctactgg tttgggtgtt    300
ttaggtttgt catggcaatc ttctccagct ttgtctgaat ggaagaaac tactttggat    360 tggttgagac agttgttggg tttatctggt caatggtctg gtgttattca agatactgct    420
tctacttcta ccttggttgc tttgatttct gctagagaaa gagctactga ttacgctttg    480
gttagaggtg gttacaagc tgaacctaaa ccattgatcg tttacgtttc tgctcatgcc    540
cattcttcag ttgataaggc tgctttgttg gctggttttg gtagagataa cattagattg    600
attccaaccg acgaaagata cgctttaaga ccagaagcct tgcaagctgc tattgaacaa    660
gatttggctg ctggtaatca accatgtgct gttgttgcta ctactggtac tactactaca    720
actgctttgg atccattaag acctgtaggt gaaattgctc aagctaatgg tttgtggttg    780
catgttgatt cagctatggc tggttctgct atgattttgc cagaatgtag atggatgtgg    840
gatggtattg aattggctga ttctgttgtt gttaacgccc ataagtggtt gggtgttgct    900
tttgattgct ctatctacta cgttagagat ccacaacact tgatcagagt gatgtctact    960
aatccatcct acttgcaatc agctgttgat ggtgaagtta agaacttgag agattggggt   1020
attccattgg gtagaagatt tagagctttg aagttgtggt ttatgttgag atccgaaggt   1080
gttgatgcat tgcaagctag attgagaaga gatttggata tgctcaatg gttggctgga   1140 caagttgaag ctgctgctga atgggaagtt ttggctccag ttcaattgca aaccttgtgc   1200
attagacata gaccagcagg tttggaaggt gaagccttgg atgctcatac aaaaggttgg   1260
gctgaaagat tgaatgcttc tggtgctgct tatgttactc cagctacttt agatggaaga   1320
tggatggtta gagtttccat tggtgcttta ccaactgaaa gaggtgacgt tcaaagattg   1380
tgggctagat tgcaagatgt tatcaagggt tga                                 1413
```

<210> SEQ ID NO 10
<211> LENGTH: 370
<212> TYPE: PRT
<213> ORGANISM: Saccharomyces cerevisiae

<400> SEQUENCE: 10

```
Met Ser Glu Ser Pro Met Phe Ala Ala Asn Gly Met Pro Lys Val Asn
1               5                   10                  15

Gln Gly Ala Glu Glu Asp Val Arg Ile Leu Gly Tyr Asp Pro Leu Ala
            20                  25                  30

Ser Pro Ala Leu Leu Gln Val Gln Ile Pro Ala Thr Pro Thr Ser Leu
        35                  40                  45

Glu Thr Ala Lys Arg Gly Arg Arg Glu Ala Ile Asp Ile Thr Gly
    50                  55                  60

Lys Asp Asp Arg Val Leu Val Ile Val Gly Pro Cys Ser Ile His Asp
65                  70                  75                  80

Leu Glu Ala Ala Gln Glu Tyr Ala Leu Arg Leu Lys Lys Leu Ser Asp
                85                  90                  95

Glu Leu Lys Gly Asp Leu Ser Ile Ile Met Arg Ala Tyr Leu Glu Lys
            100                 105                 110

Pro Arg Thr Thr Val Gly Trp Lys Gly Leu Ile Asn Asp Pro Asp Val
        115                 120                 125
```

Asn Asn Thr Phe Asn Ile Asn Lys Gly Leu Gln Ser Ala Arg Gln Leu
            130                 135                 140

Phe Val Asn Leu Thr Asn Ile Gly Leu Pro Ile Gly Ser Glu Met Leu
145                 150                 155                 160

Asp Thr Ile Ser Pro Gln Tyr Leu Ala Asp Leu Val Ser Phe Gly Ala
                165                 170                 175

Ile Gly Ala Arg Thr Glu Ser Gln Leu His Arg Glu Leu Ala Ser
            180                 185                 190

Gly Leu Ser Phe Pro Val Gly Phe Lys Asn Gly Thr Asp Gly Thr Leu
            195                 200                 205

Asn Val Ala Val Asp Ala Cys Gln Ala Ala His Ser His His Phe
210                 215                 220

Met Gly Val Thr Leu His Gly Val Ala Ala Ile Thr Thr Lys Gly
225                 230                 235                 240

Asn Glu His Cys Phe Val Ile Leu Arg Gly Gly Lys Lys Gly Thr Asn
                245                 250                 255

Tyr Asp Ala Lys Ser Val Ala Glu Ala Lys Ala Gln Leu Pro Ala Gly
            260                 265                 270

Ser Asn Gly Leu Met Ile Asp Tyr Ser His Gly Asn Ser Asn Lys Asp
            275                 280                 285

Phe Arg Asn Gln Pro Lys Val Asn Asp Val Val Cys Glu Gln Ile Ala
290                 295                 300

Asn Gly Glu Asn Ala Ile Thr Gly Val Met Ile Glu Ser Asn Ile Asn
305                 310                 315                 320

Glu Gly Asn Gln Gly Ile Pro Ala Glu Gly Lys Ala Gly Leu Lys Tyr
                325                 330                 335

Gly Val Ser Ile Thr Asp Ala Cys Ile Gly Trp Glu Thr Thr Glu Asp
            340                 345                 350

Val Leu Arg Lys Leu Ala Ala Ala Val Arg Gln Arg Glu Val Asn
            355                 360                 365

Lys Lys
    370

<210> SEQ ID NO 11
<211> LENGTH: 1113
<212> TYPE: DNA
<213> ORGANISM: Saccharomyces cerevisiae

<400> SEQUENCE: 11

```
atgagtgaat ctccaatgtt cgctgccaac ggcatgccaa aggtaaatca aggtgctgaa    60
gaagatgtca gaattttagg ttacgaccca ttagcttctc cagctctcct tcaagtgcaa   120
atcccagcca caccaacttc tttggaaact gccaagagag gtagaagaga agctatagat   180
attattaccg gtaaagacga cagagttctt gtcattgtcg gtccttgttc catccatgat   240
ctagaagccg ctcaagaata cgctttgaga ttaaagaaat tgtcagatga attaaaaggt   300
gatttatcca tcattatgag agcatacttg gagaagccaa gaacaaccgt cggctggaaa   360
ggtctaatta tgacccctga tgttaacaac actttcaaca tcaacaaggg tttgcaatcc   420
gctagacaat tgtttgtcaa cttgacaaat atcggtttgc caattggttc tgaaatgctt   480
gataccattt ctcctcaata cttggctgat ttggtctcct tcggtgccat tggtgccaga   540
accaccgaat ctcaactgca cagagaattg gcctccggtt tgtctttccc agttggtttc   600
aagaacggta ccgatggtac cttaaatgtt gctgtggatg cttgtcaagc cgctgctcat   660
tctcaccatt tcatgggtgt tactttgcat ggtgttgctg ctatcaccac tactaagggt   720
```

```
aacgaacact gcttcgttat tctaagaggt ggtaaaaagg gtaccaacta cgacgctaag      780
tccgttgcag aagctaaggc tcaattgcct gccggttcca acggtctaat gattgactac      840
tctcacggta actccaataa ggatttcaga aaccaaccaa aggtcaatga cgttgtttgt      900
gagcaaatcg ctaacggtga aaacgccatt accggtgtca tgattgaatc aaacatcaac      960
gaaggtaacc aaggcatccc agccgaaggt aaagccggct tgaaatatgg tgtttccatc     1020
actgatgctt gtataggttg ggaaactact gaagacgtct tgaggaaatt ggctgctgct     1080
gtcagacaaa gaagagaagt taacaagaaa tag                                  1113
```

<210> SEQ ID NO 12
<211> LENGTH: 196
<212> TYPE: PRT
<213> ORGANISM: Coptis japonica

<400> SEQUENCE: 12

```
Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65                  70                  75                  80

Ile Thr Gly Asp Gly Glu Gly Ser Ile Leu Asp Met Thr Phe Pro
                85                  90                  95

Pro Gly Gln Phe Pro His His Tyr Arg Glu Lys Phe Val Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145                 150                 155                 160

Pro Glu Phe Ala Lys Ile Val Lys Pro Leu Ile Asp Thr Val Pro Leu
                165                 170                 175

Ala Ile Met Ser Glu Ala Ile Ala Lys Val Val Leu Glu Asn Lys His
            180                 185                 190

Lys Ser Ser Glu
        195
```

<210> SEQ ID NO 13
<211> LENGTH: 591
<212> TYPE: DNA
<213> ORGANISM: Coptis japonica

<400> SEQUENCE: 13

```
atgagaatgg aagtcgtctt ggtcgttttc ttgatgttca ttggtactat caactgcgaa       60
agattgatct tcaatggtag accttttgttg cacagagtta ccaaagaaga aaccgttatg     120
ttgtaccacg aattggaagt tgctgcttct gctgatgaag tttggtctgt tgaaggttct      180
ccagaattgg gtttacattt gccagatttg ttgccagctg gtattttttgc caagttcgaa     240 attactggtg atggtggtga aggttccatt ttggatatga cttttccacc aggtcaattc      300
```

```
ccacatcatt acagagaaaa gttcgtcttt tcgaccaca agaacagata caagttggtc      360
gaacaaatcg atggtgattt cttcgatttg ggtgttactt actacatgga caccattaga      420
gttgttgcta ctggtccaga ttcttgcgtt attaagtcta ctactgaata ccacgtcaag      480
ccagaatttg ctaaaatcgt taagccattg atcgataccg ttccattggc tattatgtct      540
gaagctattg ccaaggttgt cttggaaaac aaacacaagt catctgaatg a               591
```

<210> SEQ ID NO 14
<211> LENGTH: 178
<212> TYPE: PRT
<213> ORGANISM: Coptis japonica

<400> SEQUENCE: 14

```
Met Glu Arg Leu Ile Phe Asn Gly Arg Pro Leu Leu His Arg Val Thr
1               5                   10                  15

Lys Glu Glu Thr Val Met Leu Tyr His Glu Leu Glu Val Ala Ala Ser
            20                  25                  30

Ala Asp Glu Val Trp Ser Val Glu Gly Ser Pro Glu Leu Gly Leu His
        35                  40                  45

Leu Pro Asp Leu Leu Pro Ala Gly Ile Phe Ala Lys Phe Glu Ile Thr
    50                  55                  60

Gly Asp Gly Gly Glu Gly Ser Ile Leu Asp Met Thr Phe Pro Pro Gly
65                  70                  75                  80

Gln Phe Pro His His Tyr Arg Glu Lys Phe Val Phe Asp His Lys
                85                  90                  95

Asn Arg Tyr Lys Leu Val Glu Gln Ile Asp Gly Asp Phe Phe Asp Leu
            100                 105                 110

Gly Val Thr Tyr Tyr Met Asp Thr Ile Arg Val Val Ala Thr Gly Pro
        115                 120                 125

Asp Ser Cys Val Ile Lys Ser Thr Thr Glu Tyr His Val Lys Pro Glu
    130                 135                 140

Phe Ala Lys Ile Val Lys Pro Leu Ile Asp Thr Val Pro Leu Ala Ile
145                 150                 155                 160

Met Ser Glu Ala Ile Ala Lys Val Val Leu Glu Asn Lys His Lys Ser
                165                 170                 175

Ser Glu
```

<210> SEQ ID NO 15
<211> LENGTH: 537
<212> TYPE: DNA
<213> ORGANISM: Coptis japonica

<400> SEQUENCE: 15

```
atggaaagat tgatcttcaa tggtagacct ttgttgcaca gagttaccaa agaagaaacc       60
gttatgttgt accacgaatt ggaagttgct gcttctgctg atgaagtttg gtctgttgaa      120
ggttctccag aattgggttt acatttgcca gatttgttgc cagctggtat tttttgccaag     180 ttcgaaatta ctggtgatgg tggtgaaggt tccatttggg atatgacttt ccaccaggt      240 caattcccac atcattacag agaaaagttc gtcttttttcg accacaagaa cagatacaag     300
ttggtcgaac aaatcgatgg tgatttcttc gatttgggtg ttacttacta catggacacc      360
attagagttg ttgctactgg tccagattct tgcgttatta gtctactac tgaataccac      420 gtcaagccag aatttgctaa atcgttaag ccattgatcg ataccgttcc attggctatt      480
atgtctgaag ctattgccaa ggttgtcttg gaaacaaaac acaagtcatc tgaatga        537
```

<210> SEQ ID NO 16
<211> LENGTH: 200
<212> TYPE: PRT
<213> ORGANISM: Coptis japonica

<400> SEQUENCE: 16

Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65                  70                  75                  80

Ile Thr Gly Asp Gly Gly Glu Gly Ser Ile Leu Asp Met Thr Phe Pro
                85                  90                  95

Pro Gly Gln Phe Pro His His Tyr Arg Glu Lys Phe Val Phe Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145                 150                 155                 160

Pro Glu Phe Ala Lys Ile Val Lys Pro Leu Ile Asp Thr Val Pro Leu
                165                 170                 175

Ala Ile Met Ser Glu Ala Ile Ala Lys Val Val Leu Glu Asn Lys His
            180                 185                 190

Lys Ser Ser Glu His Asp Glu Leu
        195                 200

<210> SEQ ID NO 17
<211> LENGTH: 603
<212> TYPE: DNA
<213> ORGANISM: Coptis japonica

<400> SEQUENCE: 17
atgagaatgg aagtcgtctt ggtcgttttc ttgatgttca ttggtactat caactgcgaa      60
agattgatct tcaatggtag acctttgttg cacagagtta ccaaagaaga aaccgttatg     120
ttgtaccacg aattggaagt tgctgcttct gctgatgaag tttggtctgt tgaaggttct     180
ccagaattgg gtttacattt gccagatttg ttgccagctg gtattttgc caagttcgaa      240
attactggtg atggtggtga aggttccatt ttggatatga cttttccacc aggtcaattc     300
ccacatcatt acagagaaaa gttcgtcttt ttcgaccaca gaacagata caagttggtc      360
gaacaaatcg atggtgattt cttcgatttg ggtgttactt actacatgga caccattaga     420
gttgttgcta ctggtccaga ttcttgcgtt attaagtcta ctactgaata ccacgtcaag     480
ccagaatttg ctaaaatcgt taagccattg atcgataccg ttccattggc tattatgtct     540
gaagctattg ccaaggttgt cttggaaaac aaacacaagt catctgaaca tgatgaattg     600
tga                                                                   603

<210> SEQ ID NO 18
<211> LENGTH: 196
<212> TYPE: PRT
<213> ORGANISM: Coptis japonica

<400> SEQUENCE: 18

```
Met Arg Met Glu Val Val Leu Val Val Phe Leu Met Phe Ile Gly Thr
1               5                   10                  15
Ile Asn Cys Glu Arg Leu Ile Phe Asn Gly Arg Pro Leu Leu His Arg
            20                  25                  30
Val Thr Lys Glu Glu Thr Val Met Leu Tyr His Glu Leu Glu Val Ala
        35                  40                  45
Ala Ser Ala Asp Glu Val Trp Ser Val Glu Gly Ser Pro Glu Leu Gly
    50                  55                  60
Leu His Leu Pro Asp Leu Leu Pro Ala Gly Ile Phe Ala Lys Phe Glu
65                  70                  75                  80
Ile Thr Gly Asp Gly Gly Glu Gly Ser Ile Leu Asp Met Thr Phe Pro
                85                  90                  95
Pro Gly Gln Phe Pro His His Tyr Arg Glu Lys Phe Val Phe Phe Asp
            100                 105                 110
His Lys Asn Arg Tyr Lys Leu Val Glu Gln Ile Asp Gly Asp Phe Phe
        115                 120                 125
Asp Leu Gly Val Thr Tyr Tyr Met Asp Thr Ile Arg Val Val Ala Thr
    130                 135                 140
Gly Pro Asp Ser Cys Val Ile Lys Ser Thr Thr Glu Tyr His Val Lys
145                 150                 155                 160
Pro Glu Phe Ala Lys Ile Val Lys Pro Leu Ile Asp Thr Val Pro Leu
                165                 170                 175
Ala Asp Met Ser Glu Ala Ile Ala Lys Val Val Leu Glu Asn Lys His
            180                 185                 190
Lys Ser Ser Glu
        195
```

<210> SEQ ID NO 19
<211> LENGTH: 591
<212> TYPE: DNA
<213> ORGANISM: Coptis japonica

<400> SEQUENCE: 19

| | | |
|---|---|---|
| atgagaatgg aagtcgtctt ggtcgttttc ttgatgttca ttggtactat caactgcgaa | 60 |
| agattgatct caatggtag acctttgttg cacagagtta ccaaagaaga aaccgttatg | 120 |
| ttgtaccacg aattggaagt tgctgcttct gctgatgaag tttggtctgt tgaaggttct | 180 |
| ccagaattgg gtttacattt gccagatttg ttgccagctg gtattttttgc caagttcgaa | 240 |
| attactggtg atggtggtga aggttccatt ttggatatga cttttccacc aggtcaattc | 300 |
| ccacatcatt acagagaaaa gttcgtcttt tcgaccaca agaacagata caagttggtc | 360 |
| gaacaaatcg atggtgattt cttcgatttg gtgttactt actacatgga caccattaga | 420 |
| gttgttgcta ctggtccaga ttcttgcgtt attaagtcta ctactgaata ccacgtcaag | 480 |
| ccagaatttg ctaaaatcgt taagccattg atcgataccg ttccattggc tgatatgtct | 540 |
| gaagctattg ccaaggttgt cttggaaaac aaacacaagt catctgaatg a | 591 |

<210> SEQ ID NO 20
<211> LENGTH: 200
<212> TYPE: PRT
<213> ORGANISM: Coptis japonica

<400> SEQUENCE: 20

Met Arg Met Glu Val Val Leu Val Val Phe Leu Met Phe Ile Gly Thr
1               5                   10                  15

Ile Asn Cys Glu Arg Leu Ile Phe Asn Gly Arg Pro Leu Leu His Arg
            20                  25                  30

Val Thr Lys Glu Glu Thr Val Met Leu Tyr His Glu Leu Glu Val Ala
        35                  40                  45

Ala Ser Ala Asp Glu Val Trp Ser Val Glu Gly Ser Pro Glu Leu Gly
    50                  55                  60

Leu His Leu Pro Asp Leu Leu Pro Ala Gly Ile Phe Ala Lys Phe Glu
65              70                  75                  80

Ile Thr Gly Asp Gly Glu Gly Ser Ile Leu Asp Met Thr Phe Pro
                85                  90                  95

Pro Gly Gln Phe Pro His His Tyr Arg Glu Lys Phe Val Phe Phe Asp
            100                 105                 110

His Lys Asn Arg Tyr Lys Leu Val Glu Gln Ile Asp Gly Asp Phe Phe
        115                 120                 125

Asp Leu Gly Val Thr Tyr Tyr Met Asp Thr Ile Arg Val Val Ala Thr
    130                 135                 140

Gly Pro Asp Ser Cys Val Ile Lys Ser Thr Thr Glu Tyr His Val Lys
145             150                 155                 160

Pro Glu Phe Ala Lys Ile Val Lys Pro Leu Ile Asp Thr Val Pro Leu
                165                 170                 175

Ala Asp Met Ser Glu Ala Ile Ala Lys Val Val Leu Glu Asn Lys His
            180                 185                 190

Lys Ser Ser Glu His Asp Glu Leu
        195                 200

<210> SEQ ID NO 21
<211> LENGTH: 603
<212> TYPE: DNA
<213> ORGANISM: Coptis japonica

<400> SEQUENCE: 21
atgagaatgg aagtcgtctt ggtcgttttc ttgatgttca ttggtactat caactgcgaa     60
agattgatct tcaatggtag acctttgttg cacagagtta ccaaagaaga aaccgttatg    120
ttgtaccacg aattggaagt tgctgcttct gctgatgaag tttggtctgt tgaaggttct    180
ccagaattgg gtttacattt gccagatttg ttgccagctg gtattttgc caagttcgaa    240
attactggtg atggtggtga aggttccatt ttggatatga cttttccacc aggtcaattc    300
ccacatcatt acagagaaaa gttcgtcttt ttcgaccaca gaacagata caagttggtc    360
gaacaaatcg atggtgattt cttcgatttg ggtgttactt actacatgga caccattaga    420
gttgttgcta ctggtccaga ttcttgcgtt attaagtcta ctactgaata ccacgtcaag    480
ccagaatttg ctaaaatcgt taagccattg atcgataccg ttccattggc tgatatgtct    540
gaagctattg ccaaggttgt cttggaaaac aaacacaagt catctgaaca tgatgaattg    600
tga                                                                 603

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

His Asp Glu Leu
1

NORCOCLAURINE SYNTHASES WITH INCREASED ACTIVITY

This application is a U.S. national phase application of International Patent Application No. PCT/EP2018/066153 filed on Jun. 18, 2018, which claims the benefit of Danish Patent Application PA201770474 filed on Jun. 16, 2017 and Danish Patent Application No. PA201770533 filed on Jun. 30, 2017.

FIELD OF THE INVENTION

The invention relates to norcoclaurine synthases having an increased catalysation of the condensation of 4-HPAA and dopamine to (S)-norcoclaurine and/or 3,4-DhPAA and dopamine to (S)-norlaudanosoline.

STATEMENT REGARDING SEQUENCE LISTING

A computer readable form of the Sequence Listing is filed with this application by electronic submission and is incorporated into this application by reference in its entirety. The sequence listing submitted herewith is contained in the text file created Jan. 29, 2024, entitled "19-2316-WO-US_Sequence-Listing_ST25.txt" and 34,428 bytes in size.

BACKGROUND OF THE INVENTION

Norcoclaurine synthase (NCS) is an enzyme involved in committing and rate limiting steps of benzylisoquinoline (BIA) biosynthesis. The two precursor molecules 4-hydroxy-phyenylacetaldehyde (4-HPAA) and dopamine are condensed in a Pictet-Spengler reaction to form (S)-norcoclaurine. Norcoclaurine synthase can also use 3,4-dihydroxy-acetaldehyde (3,4-DHPAA) as substrate in place of 4-HPAA for the formation of (S)-norlaudanosoline.

Among the known norcoclaurine synthases the homolog from *Thalictrum flavum* is best studied. Both biochemical and structural data are available for this enzyme. NCS is a catalytically inefficient enzyme with $K_M$ values in the double-digit mM range. Low activity is confirmed in yeast strains producing norcoclaurine. The molar concentration of the produced norcoclaurine is about 100-fold lower than the concentration of the precursor dopamine (Narcross, et al. Trends Biotechnol. 34, 228-241 (2016) & DeLoache, W. C. et al. Nat. Chem. Biol. 11, 465-471 (2015))

A heterologous yeast cell that produces norcoclaurine is e.g. known from U.S. Pat. No. 8,975,063, which disclose wildtype norcoclaurine synthase isolated from *Thalictrum flavum* and wildtype norcoclaurine synthase isolated from *Papaverum somniferum*.

Prior art describes that norcoclaurine synthase activity so far obtained in yeast is too low for driving an efficient and commercially attractive benzylisoquinoline pathway as an alternative to e.g. plant cells. Thus, there is a need for engineering an improved norcoclaurine synthase capable of increased activity in for example, a yeast strain.

SUMMARY OF THE INVENTION

To identify norcoclaurine synthases with increased activity in heterologous host cells such as yeast, the inventors have expressed several NCS homologs on episomal vectors gathered from different species and analyzed norcoclaurine production in the supernatant of the cultures.

Codon optimized NCS from the flower *Coptis japonica* was identified as the most active enzyme. Further enzyme engineering approaches to improve NCS functionality where made, leading to identification of mutation sites across the protein, which increase activity and/or substrate selectivity.

The inventors identified substrate-binding domains in which mutations enhanced NCS activity.

Thus, one aspect of the invention relates to norcoclaurine synthases comprising a substrate binding amino acid sequence, which is at least 50% similar to the substrate binding amino acid sequence SEQ ID NO: 4 and/or SEQ ID NO: 5, and wherein the substrate binding amino acid sequence(s) comprise one or more mutations increasing the norcoclaurine synthase activity compared to wild type.

In one aspect of the invention relates to norcoclaurine synthases comprising an amino acid sequence which is at least 40% identical to the amino acid sequence given in SEQ ID No: 1, and which has one or more site-specific mutation at position 73, 75, 77, 82, 99, 114, 141, 142, 147, 152, 174 and/or 178 in the count according to SEQ ID No: 1.

In another aspect, the present invention also relates to mutated norcoclaurine synthase amino acid sequences originating from *Coptis japonica* having an increased catalysation, when compared to the wild type synthase, of the condensation of 4-HPAA and dopamine to (S)-norcoclaurine and/or 3,4-DHPAA and dopamine to (S)-norlaudanosoline. The mutation may for example be present in the substrate-binding amino acid sequences.

DETAILED DESCRIPTION OF THE INVENTION

For driving an efficient and commercially viable benzylisoquinoline pathway in heterologous host cells, currently known wild type norcoclaurine synthases like, for example those sourced from *Coptis japonica* or *Thalictrum flavum* do not provide a high enough activity via the Pictet-Spengler reaction to form (S)-norcoclaurine in sufficient quantities.

Many benzylisoquinoline alkaloids are of great medical interest because of their pharmacological activity, such as, for example, the antibiotic sanguinarine, the muscle relaxants papaverine and tubocurarine and the analgesics codeine and morphine.

Galanie S. et al., Science 2015 disclosed a complete biosynthesis of opioids through enzyme discovery, enzyme engineering, and pathway and strain optimization to realize full opiate biosynthesis in yeast, thereby enabling obtaining all of the following end-products: Thebaine, Oripavine, Neopinone, Codeinone, Hydrocodone, Morphine, Oxycodone and Codeine. Furthermore, DeLoache, W. C. et al., Nature Chemical Biology 2015 disclosed the pathway to fully reconstitute the seven-enzyme pathway from L-tyrosine to (S)-reticuline, thereby enabling obtaining all of the following end-products: Noscapine, Berberine, Sanguinarine, Tubocurarine and Papaverine. Thus, the present invention relates to improved production of any of the above-mentioned opioids in yeast via mutated norcoclaurine synthase as described herein.

The invention describes the engineering of norcoclaurine synthase having site-specific mutations for increased activity in heterologous host cells. These site-specific mutations may additionally be transferred between species due to their unique positions in the norcoclaurine synthase, because the mutation sites are sited in putative substrate binding domains whose relative positions will be conserved between different NCS enzymes, such as but not limited to conserved domains amongst species. The conserved domains can for example be the helix structures and/or loop binding sites identified by the inventors.

In one aspect the invention relates to a norcoclaurine synthase comprising a substrate-binding amino acid sequence, which is at least 50% similar or 20% identical to the substrate binding amino acid sequence SEQ ID NO: 4 and/or SEQ ID NO: 5, and wherein the substrate binding amino acid sequence(s) comprise one or more mutations increasing the norcoclaurine synthase activity compared to wild type. In some embodiments, the substrate binding amino acid sequence identified by the inventors and disclosed herein is an amino acid sequence which is at least 50% similar or 20% identical to the amino acid sequence SEQ ID NO: 4.

In some embodiments, another substrate binding amino acid sequence identified is an amino acid sequence, which is at least 50% similar or 20% identical to the amino acid sequence SEQ ID NO: 5. Both of these substrate-binding amino acid sequences are engineered to comprise one or more mutations increasing the norcoclaurine synthase activity compared to wild type.

In the present context, the term substrate binding amino acid sequence, substrate binding site or catalytic site may be used interchangeably.

Norcoclaurine Synthases (NCS)

Norcoclaurine synthases (NCS) are enzymes capable of catalysing the formation of (S)-norcoclaurine and (S)-norlaudonosoline via condensation of 4-HPAA and dopamine (for norcoclaurine) or 3,4-DHPAA and dopamine (for norlaudonosoline, see FIG. 1).

This enzyme belongs to the family of lyases, specifically the hydrolyases, which cleave carbon-oxygen bonds. The systematic name of this enzyme class is 4-hydroxyphenylacetaldehyde hydro-lyase. Other names in common use include (S)-norlaudanosoline synthase, and 4-hydroxyphenylacetaldehyde hydro-lyase. This enzyme participates in benzylisoquinoline alkaloid (BIA) biosynthesis.

The NCS of the present invention have amino acid sequences, which are at least 40% identical to the amino acid sequence given in SEQ ID No: 1. However, the NCS of the invention do not relate to the wild type NCS in SEQ ID NO: 1 per se.

In some embodiments, the mutation(s) may comprise one or more site-specific mutations corresponding to position 2, 4, or 6 in the count according to SEQ ID No: 4 and/or position 2, or 6 in the count according to SEQ ID No: 5. In some embodiments, the mutation(s) may further comprise one or more site-specific mutation corresponding to position 73, 75, 77, 174 and/or 178 in the count according to SEQ ID No: 3.

The NCS disclosed herein have an increased catalysation of the condensation of 4-HPAA and dopamine to (S)-norcoclaurine and/or 3,4-DhPAA and dopamine to (S)-norlaudanosoline, when compared to the wild type NCS in SEQ ID NO: 1 per se.

NCS molecules of the invention have amino acid sequences, which are at least 40% identical to the amino acid sequence given in SEQ ID NO: 1. NCS of the invention may comprise substrate binding domains as described. However, NCS disclosed herein do not relate to the wild type NCS in SEQ ID NO: 1 per se because NCS disclosed herein have an increased catalysation of the condensation of 4-HPAA and dopamine to (S)-norcoclaurine and/or 3,4-DhPAA and dopamine to (S)-norlaudanosoline, when compared to the wild type NCS in SEQ ID NO: 1.

Accordingly, NCS variants disclosed herein are more suitable for commercial benzylisoquinoline alkaloid biosynthesis given their improved activity.

As used herein, the term "increased catalysation" means increasing the speed of the condensation compared to the wild type NCS in SEQ ID NO: 1 per se. Terms like "catalytic activity", "turnover", "activity" could be used interchangeably.

Mutation Positions

The inventors disclose specific mutations in NCS derived from *Coptis japonica* that results in increased activity of the condensation process. Amino acid exchanges in positions corresponding to positions 73, 75, 77, 82, 99, 114, 141, 142, 147, 152, 174 and/or 178 of SEQ ID No: 1 provided the best increase in formation of S-Norcoclaurine (µg/ml), when compared to the wild type—see Table 8.

Thus, in one or more exemplary embodiments, the invention relates to a norcoclaurine synthase comprising an amino acid sequence which is at least 40% identical to the amino acid sequence given in SEQ ID No: 1, and which has one or more site-specific mutations corresponding to position 73, 75, 77, 82, 99, 114, 141, 142, 147, 152, 174 and/or 178 in the count according to SEQ ID No: 1.

The site-specific mutation corresponding to position 73 in the count according to SEQ ID No: 1 may preferably be Proline (P). Thus, in one or more exemplary embodiments, the invention relates to a norcoclaurine synthase, which has the amino acid Proline (P) corresponding to position 2 in the count according to SEQ ID No: 4. In one or more exemplary embodiments, the site-specific mutation is A73P in the count according to SEQ ID No: 1. In one or more exemplary embodiments, the site-specific mutation is A2P in the count according to SEQ ID No: 4.

In one or more exemplary embodiments the site-specific mutation corresponding to position 75 in the count according to SEQ ID No: 1 is Leucine (L) or Lysine (K). Thus, in one or more exemplary embodiments, the invention relates to a norcoclaurine synthase, which has the amino acid Leucine (L) or Lysine (K) corresponding to position 4 in the count according to SEQ ID No: 4. In one or more exemplary embodiments, the site-specific mutation is I75K or I75L in the count according to SEQ ID No: 1. In one or more exemplary embodiments, the site-specific mutation is I4K or I4L in the count according to SEQ ID No: 4.

The site-specific mutation corresponding to position 77 in the count according to SEQ ID No: 1 may preferably be Serine (S), Threonine (T) or Glutamic Acid (E). In one or more exemplary embodiments, the site-specific mutation is A77S, A77T or A77E in the count according to SEQ ID No: 1.

In one or more exemplary embodiments, the site-specific mutation is A6S, A6T or A6E in the count according to SEQ ID No: 4.

The site-specific mutation corresponding to position 82 in the count according to SEQ ID No: 1 may preferably be Valine (V). In one or more exemplary embodiments, the site-specific mutation is T82V in the count according to SEQ ID No: 1.

The site-specific mutation corresponding to position 99 in the count according to SEQ ID No: 1 may preferably be Lysine (K) or Arginine (R). In one or more exemplary embodiments, the site-specific mutation is Q99K or Q99R in the count according to SEQ ID No: 1.

The site-specific mutation corresponding to position 141 in the count according to SEQ ID No: 1 may preferably be Isoleucine (I). In one or more exemplary embodiments, the site-specific mutation is V141I the count according to SEQ ID No: 1.

The site-specific mutation corresponding to position 142 in the count according to SEQ ID No: 1 may preferably be Isoleucine (I). In one or more exemplary embodiments, the site-specific mutation is V142I the count according to SEQ ID No: 1.

The site-specific mutation corresponding to position 147 in the count according to SEQ ID No: 1 may preferably be Asparagine (N). In one or more exemplary embodiments, the site-specific mutation is D147N the count according to SEQ ID No: 1.

The site-specific mutation corresponding to position 152 in the count according to SEQ ID No: 1 may preferably be Arginine (R). In one or more exemplary embodiments, the site-specific mutation is K152R the count according to SEQ ID No: 1.

The site-specific mutation corresponding to position 174 in the count according to SEQ ID No: 1 may preferably be Glycine (G) or Glutamic Acid (E). In one or more exemplary embodiments, the site-specific mutation is V174G or V174E in the count according to SEQ ID No: 1. Thus, in one or more exemplary embodiments, the invention relates to a norcoclaurine synthase, which has the amino acid Glycine (G) or Glutamic Acid (E) corresponding to position 2 in the count according to SEQ ID No: 5.

In one or more exemplary embodiments, the site-specific mutation is V2G or V2E in the count according to SEQ ID No: 5.

The site-specific mutation corresponding to position 178 in the count according to SEQ ID No: 1 may preferably be Alanine (A), Serine (S) or Aspartic Acid (D). In one embodiment, the site-specific mutation is I178A, I178S or I178D in the count according to SEQ ID No: 1. Thus, in one embodiment, the invention relates to a norcoclaurine synthase, which has the amino acid Alanine (A), Serine (S) or Aspartic Acid (D) corresponding to position 6 in the count according to SEQ ID No: 5. In one embodiment, the site-specific mutation is I6A, I6S or I6D in the count according to SEQ ID No: 5.

The site-specific mutations described above may be combined in double, triple or further mutations to enhance the effect of the norcoclaurine synthase. The skilled addressee can test these combinations by the methods disclosed in the Examples, which are intended to provide non-limiting examples of mutations and combinations of mutations. All such combinations are individual embodiments of the present invention regardless of the corresponding position count according to SEQ ID NO: 1-5, and various of these embodiments are described below.

In one or more exemplary embodiments, the invention relates to a norcoclaurine synthase, which has the amino acid Proline (P) corresponding to position 73 and Glutamic Acid (E) corresponding to position 77 in the count according to SEQ ID No: 1, e.g. A73P/A77E.

In one or more exemplary embodiments, the invention relates to a norcoclaurine synthase, which has the amino acid Proline (P) corresponding to position 2 and Leucine (K) or Lysine (L) corresponding to position 4 in the count according to SEQ ID No: 4, e.g. A2P/I4K, A2P/I4L.

In one or more exemplary embodiments, the invention relates to a norcoclaurine synthase, which has the amino acid Arginine (R) corresponding to position 152 and Glutamic Acid (E) corresponding to position 174 in the count according to SEQ ID No: 1, e.g. K152R/V174E.

In one or more exemplary embodiments, the invention relates to a norcoclaurine synthase, which has the amino acid Proline (P) corresponding to position 2 and Serine (S), Threonine (T) or Glutamic Acid (E) corresponding to position 6 in the count according to SEQ ID No: 4, e.g. A2P/A6S, A2P/A6T, or A2P/A6E.

In one or more exemplary embodiments, the invention relates to a norcoclaurine synthase, which has the amino acid Glutamic Acid (E) corresponding to position 114 and Glutamic Acid (E) corresponding to position 174 in the count according to SEQ ID No: 1, e.g. K114E/V174E.

In one or more exemplary embodiments, the invention relates to a norcoclaurine synthase, which has the amino acid Leucine (K) or Lysine (L) corresponding to position 4 and Serine (S), Threonine (T) or Glutamic Acid (E) corresponding to position 6 in the count according to SEQ ID No: 4, e.g. I4K/A6S, I4K/A6T, I4K/A6E, I4L/A6S, I4L/A6T, or I4L/A6E.

In one or more exemplary embodiments, the invention relates to a norcoclaurine synthase, which has the amino acid Glutamic Acid (E) corresponding to position 114 and Glycine (G) corresponding to position 174 in the count according to SEQ ID No: 1, e.g. V174G/K114E.

In one or more exemplary embodiments, the invention relates to a norcoclaurine synthase, which has the amino acid Proline (P) corresponding to position 2, Leucine (K) or Lysine (L) corresponding to position 4 and Serine (S), Threonine (T) or Glutamic Acid (E) corresponding to position 6 in the count according to SEQ ID No: 4, A2P/I4K/A6S, A2P/I4K/A6T, A2P/I4K/A6E, A2P/I4L/A6S, A2P/I4L/A6T, or A2P/I4L/A6E.

In one or more exemplary embodiments, the invention relates to a norcoclaurine synthase, which has the amino acid Arginine (R) corresponding to position 152 and Glycine (G) corresponding to position 174 in the count according to SEQ ID No: 1, e.g. V174G/K152R.

In one or more exemplary embodiments, the norcoclaurine synthase may have site-specific mutations at both position 2 and 6 in the count according to SEQ ID No: 5.

In one or more exemplary embodiments, the invention relates to a norcoclaurine synthase, which has the amino acid Arginine (R) corresponding to position 152 and Alanine (A) or Aspartic Acid (D) corresponding to position 178 in the count according to SEQ ID No: 1, e.g. I178D/K152R or I178A/K152R.

Thus, in one or more exemplary preferred embodiments, position 2 and 6 in the count according to SEQ ID No: 5 has the amino acid Glycine (G) or Glutamic Acid (E) corresponding to position 2 and Alanine (A), Serine (S) or Aspartic Acid (D) corresponding to position 6, e.g. V2G/I6A, V2G/I6S, V2G/I6D, V2E/I6A, V2E/I6S, or V2E/I6D in the count according to SEQ ID No: 5.

Other combinations like for example A73P/V174G, A73P/V174E, A66S/V174G, A66S/V174E in the count according to SEQ ID No: 1 is also an embodiment of the invention.

In one or more exemplary presently preferred embodiments, the combinatorial mutations may be selected from the group consisting of I178D+I75L, I178D+I75K, I178D+A77S, I178D+V174Q, A73P+A77E and A77T+I178D in the count according to SEQ ID No: 1.

In one or more exemplary presently preferred embodiments, the combinatorial mutations may be selected from the group consisting of K114E/V174E, K152R/V174E, V174G/K152R, V174G/K114E, I178A/152R, I178D/K152R, I178D/174E/K152R, I178D/K114E/K152R, I178D/

V174E/Q99K, I178D/V174Q/Q99K, I178D/V174E/Q99R, and I178D/V174Q/Q99R in the count according to SEQ ID No: 1.

In one or more exemplary presently preferred embodiments, the combinatorial mutations may be selected from the group consisting of I178D+I75L, I178D+I75K, I178D+A77S, I178D+A77S+K152R, I178D+I75K+K152R, I178D+V174G+K152R+A77S, A77T+I178D, I178D+V174Q, A73P+A77E and A77T+I178D in the count according to SEQ ID No: 1.

In one or more exemplary embodiments, the invention relates to a norcoclaurine synthase, wherein the site-specific mutation is selected from the group consisting of A73P, I75L, I75K, A77S, A77E, A77T, T82V, Q99K, Q99R K114E, V141I, V142I, D147N, K152R, V174E, V174G, V174Q, V174E, I178A, I178S, I178D, I178N, I178Q, and I178T in the count according to SEQ ID No: 1.

The in Silico Predicted Flexible Loop as Substrate Binding Domain

In addition to the helical domain described below, which is predicted to interact with substrate and may be advantageously mutated to enhance such interactions, the generated homology model of C. japonica NCS also reveals a flexible loop region, which is predicted to interact with substrates.

The inventors show that this motif also contains amino acids for which mutations affect substrate binding. This loop is formed by amino acids P72-A77 in the count corresponding to SEQ ID NO: 1—equivalent to P1-A6 in the count corresponding to SEQ ID NO: 4—and is located in 3D proximity to the helix domain (SEQ ID NO: 5).

Thus, the flexible loop is also predicted to contact the substrate, based on the model of C. japonica NCS disclosed by the inventors.

In one or more presently preferred embodiments, the invention relates to mutations in this flexible loop binding domain comprising site specific mutations corresponding to position 2, 4 and 6 in the count corresponding to SEQ ID 4.

Such mutations may be advantageously combined with those from helix domain, because these two regions interact in the protein model and therefore combined mutations will have concerted effects on substrate binding The in Silico Predicted Helix Structure as Substrate Binding Motif The crystal structure of T. flavum NCS (Ilari et al. 2009, Journal of biological chemistry, 284(2), pp. 897-904), and a subsequent study (Bonamore et al. 2010, Molecules, 15(4), pp. 2070-2078) suggest an enzymatic mechanism for NCS that involves binding of 4-HPAA to the enzyme prior to dopamine (the 'HPAA-first' mechanism). An alternative mechanism has also been proposed in which dopamine binds to the enzyme prior to 4-HPAA (the 'dopamine-first' mechanism) (Lichman et al. 2015, FEBS journal, 282(6), pp. 1137-1151).

The invention relates to a norcoclaurine synthase comprising mutations in aldehyde binding pocket domains of the synthase regardless of the enzymatic mechanism.

Based on the model of C. japonica NCS disclosed by the inventors, amino acid positions V174 and I178 corresponding to SEQ ID NO: 3 (V2 and 16 in SEQ ID NO: 2) are predicted to affect the catalytic activity of NCS.

For example, the predicted location in an alpha helix with an N-terminus at the wild-type amino acid position V174 and a C-terminus corresponding to position L188. For example, position 178 of NCS contains Isoleucine. PROTOSCAN was used to rank energies of other mutations at this position and aspartic acid had the lowest energy, because of enhanced interaction with the para hydroxyl group of HPAA substrate as shown in FIG. 2.

Irrespective of the HPAA-first or dopamine-first mechanisms, this model of C. japonica NCS shows that this helix corresponding to positions 174-188 of SEQ ID NO: 3 is involved in binding of the aldehyde and/or dopamine substrates of NCS. In addition, the location of the helix corresponding to positions 174-188 of SEQ ID NO: 3 suggests that it may also gate access of aldehyde and/or dopamine substrates to the active site of NCS. Therefore, other amino acid variants of the helix corresponding to positions 174-188 in C. japonica may also affect catalytic activity.

Thus, in one or more exemplary embodiments, the present invention relates to a norcoclaurine synthase comprising an amino acid sequence forming a helix structure homologue to positions 174-188 in C. japonica, and wherein site-specific mutations in said helix structure improve the activity of the enzyme.

The invention also relates to a norcoclaurine synthase having an amino acid sequence forming a helix structure, which is at least 60% identical to the amino acid sequence given in SEQ ID No: 4, such as 65%, 70%, 75%, 80%, 85%, 95% identical. Said norcoclaurine synthase can within said helix structure further comprise at least one site-specific mutations, such as one site-specific mutation, two site-specific mutations, three site-specific mutations, four site-specific mutations or more.

In one or more exemplary embodiments, the helix structure comprises site-specific mutation(s) corresponding to position 174 and/or 178 in SEQ ID 1 (2 and 6 in SEQ ID NO: 5).

The inventors demonstrate that NCS's having mutated helical substrate binding domains with only 10 amino acid are industrial beneficial, and this domain is conserved across NCS's, which provides an effective choke point across species.

Disruption of Signal Peptide Function

Using the amino acid sequence of the C. japonica NCS as query, a signal peptide prediction was done using SignalP 4.1. (Petersen, T. N et al Nature Methods, 8:785-786, 2011). This program predicts that the first 19 amino acid of the C. japonica NCS constitute a signal peptide with a predicted cleavage site between amino acids 19 and 20 from the N-terminus. As seen in FIG. 7 Norcoclaurine production in S. cerevisiae increases dramatically, when the first 19 amino acids from the N-terminal of the C. japonica NCS are replaced by a methionine.

In one or more exemplary embodiments, the invention relates to a norcoclaurine synthase according to the present disclosure where the signal peptide function has been disrupted. This could typically be via mutations or partly removal of the signal peptide sequence. In fact, any change to the NCS that prevent the N-terminal signal peptide from working, i.e. any change that prevents translocation of the NCS into the ER lumen. Thus, the invention relates to a mutated norcoclaurine synthase having an increased catalysation when compared to the wild type synthase of the condensation of 4-HPAA and dopamine to (S)-norcoclaurine and/or 3,4-DHPAA and dopamine to (S)-norlaudanosoline comprising an amino acid sequence, which is at least 40% identical to the amino acid sequence given in SEQ ID No: 1, further comprising rendering the signal peptide non-functional.

Thus, in one or more exemplary embodiments, the invention relates to a norcoclaurine synthase according to the present disclosure further comprising replacing one or more amino acids from the N-terminal with a methionine or by mutation or removal of one or more amino acids from the signal peptide sequence or any truncation rendering the signal peptide non-functional.

The 19 amino acid truncation, see FIG. 7, deletes the predicted signal peptide sequence and therefore prevents the enzyme from entering the secretory pathway. Instead the enzyme will go to the cytosol instead.

Thus, in one or more exemplary embodiments, the invention relates to a norcoclaurine synthase according to the present disclosure further comprising replacing at least 1 amino acids from the N-terminal with a methionine, such as at least 1 amino acids, at least 2 amino acids, at least 3 amino acids, at least 4 amino acids, at least 5 amino acids, at least 6 amino acids, at least 7 amino acids, at least 8 amino acids, at least 9 amino acids, at least 10 amino acids, at least 11 amino acids, at least 12 amino acids, at least 13 amino acids, at least 14 amino acids, at least 15 amino acids, at least 16 amino acids, at least 17 amino acids, at least 18 amino acids, at least 19 amino acids, at least 20 amino acids, or more amino acids from the N-terminal with a methionine.

While the plant signal peptide is very likely to work in yeast, other sorting and retention signals might not. It is therefore very likely that the full-length C. japonica NCS expressed in yeast is excreted by vesicular transport from the ER lumen through the Golgi apparatus to the plasma membrane and thereby to the extracellular space.

Addition an ER retention signal to the NCS enzyme-HDEL (SEQ ID NO: 22)

The addition of the amino acids HDEL (SEQ ID NO: 22) to the C-terminus of a full-length C. japonica NCS has a significant positive effect of Norcoclaurine production in S. cerevisiae. The addition of the yeast ER retention signal HDEL (SEQ ID NO: 22) to the C-terminus of the CjNCS was designed to retain the enzyme in the ER/golgi and thereby prevent it from being excreted into the extracellular space.

The positive effect on Norcoclaurine production of this localization is unexpected since the enzymes that produce dopamine and 4-HPAA are believed to be cytosolic and it shows that a pool of 4-HPAA and dopamine exists not only in the cytosol, but also in the ER/golgi of S. cerevisiae.

In one or more exemplary embodiments, the invention relates to a norcoclaurine synthase according to the present disclosure, wherein the norcoclaurine synthase is held in the ER/golgi. The effect is also achievable for unmutated norcoclaurine synthase, thus in one or more exemplary embodiments, the invention relates to a norcoclaurine synthase having an increased catalysation when compared to the wild type synthase of the condensation of 4-HPAA and dopamine to (S)-norcoclaurine and/or 3,4-DHPAA and dopamine to (S)-norlaudanosoline comprising an amino acid sequence, which is at least 40% identical to the amino acid sequence given in SEQ ID No: 1 and further comprising an addition of the yeast ER retention signal HDEL to the C-terminus. Localisation will typically be shown by either N- or C-terminal tagging of the protein with a fluorescent protein, GFP, RFP or similar followed by fluorescence microscopy.

Altering the localization of the NCS, thus allows the utilization of hitherto inaccessible pools of 4-HPAA and dopamine. This more complete utilization can be beneficial for both obtaining higher titers, but also to prevent potentially harmful accumulation of precursors in organelles of S. cerevisiae by conversion into later non-toxic pathway products. Dopamine is known to be cytotoxic in S. cerevisiae.

In one or more exemplary embodiments, the invention relates to a norcoclaurine synthase according to the present disclosure, further comprising addition of the amino acids HDEL (SEQ ID NO: 22) to the C-terminus.

Coptis japonica NCS1178D with HDEL (SEQ ID NO: 22) addition

As seen in FIG. 8 below the change of the amino acid I178 to a D (isoleucine to aspartic acid) of the C. japonica sequence improves the activity of the enzyme and hence the production of norcoclaurine significantly.

Moreover, FIG. 8 also shows that the CjNCS 1178 to D amino acid change also significantly improves the activity of the C. japonica NCS version with the HDEL (SEQ ID NO: 22) addition in the C-terminus.

Again, this shows that a large and untapped pool of dopamine and 4-HPAA exists in the ER/golgi of S. cerevisiae. Since the Δ19-CjNCS and the CjNCS-HDEL (both native and I178D) exists in different compartments of the yeast cell, co-expression of both is likely to give effects on norcoclaurine production titers.

In one or more presently preferred exemplary embodiments, the invention relates to a norcoclaurine synthase comprising the site-specific mutation to Aspartic Acid (D) corresponding to position 178 in the count according to SEQ ID NO: 1, and further comprising the addition of the amino acids HDEL (SEQ ID NO: 22) to the C-terminus.

Amino Acid Sequence Identity

Sequence analysis can involve BLAST, Reciprocal BLAST, or PSI-BLAST analysis of non-redundant databases using the amino acid sequence of interest as the reference sequence. Amino acid sequence is, in some instances, deduced from the nucleotide sequence. Those polypeptides in the database that have greater than 40% sequence identity are candidates for further evaluation for suitability as polypeptide useful in the synthesis of compounds described herein. Amino acid sequence similarity allows for conservative amino acid substitutions, such as substitution of one hydrophobic residue for another or substitution of one polar residue for another. When desired, manual inspection of such candidates can be carried out in order to narrow the number of candidates to be further evaluated. Manual inspection can be performed by selecting those candidates that appear to have conserved functional domains.

Conserved regions can be identified by locating a region within the primary amino acid sequence of a polypeptide described herein that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., Nucl. Acids Res., 26:320-322 (1998); Sonnhammer et at., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some aspects, alignment of sequences from two different species can be adequate.

The polypeptides disclosed herein may exhibit at least 40% amino acid sequence identity to any of SEQ ID NOs: 1-3, such as at least 45% amino acid sequence identity, at least 50%, at least 60%, at least 70%, at least 80%, or at least 90% amino acid sequence identity. In some embodiments, the polypeptides exhibit at least 81%, 82%, 83%, 84%, 85%, 86%, 87%, 88%, 89%, 91%, 92%, 93%, 94%, 95%, 96%, 97%, 98%, or 99% amino acid sequence identity.

Identity

The term "% identity" is used herein about the relatedness between two amino acid sequences or between two nucleotide sequences.

The term "% identity" as used herein about amino acid sequences means the degree of identity in percent between two amino acid sequences obtained when using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later.

Similarity

The term "% similarity" as used herein about amino acid sequences means the degree of similarity in percent between two amino acid sequences obtained when using the Needleman-Wunsch algorithm (Needleman and Wunsch, 1970, supra) as implemented in the Needle program of the EMBOSS package (EMBOSS: The European Molecular Biology Open Software Suite, Rice et al., 2000, Trends Genet. 16: 276-277), preferably version 5.0.0 or later.

The parameters used are gap open penalty of 10, gap extension penalty of 0.5, and the EBLOSUM62 (EMBOSS version of BLOSUM62) substitution matrix. The output of Needle labeled "longest identity" (obtained using the -no-brief option) is used to calculate the percent identity follows:

100*identical amino acid residues/(Length of alignment–total number of gaps in alignment)

The output of Needle labeled "longest similarity" (obtained using the -no brief option) is used to calculate the percent similarity as follows:

100*similar amino acid residues/(Length of alignment–total number of gaps in alignment)

The protein sequences disclosed herein can further be used as a "query sequence" to perform a search against sequence databases, for example to identify other family members or related sequences. Such searches can be performed using the BLAST programs. Software for performing BLAST analyses is publicly available through the National Centre for Biotechnology Information (http://www.ncbi.nlm.nih.gov). BLASTP is used for amino acid sequences and BLASTN for nucleotide sequences. The BLAST program uses as defaults:

Cost to open gap: default=5 for nucleotides/11 for proteins
Cost to extend gap: default=2 for nucleotides/1 for proteins
Penalty for nucleotide mismatch: default=−3
Reward for nucleotide match: default=1
Expect value: default=10
Wordsize: default=11 for nucleotides/28 for megablast/3 for proteins Furthermore, the degree of local identity between the amino acid sequence query or nucleic acid sequence query and the retrieved homologous sequences is determined by the BLAST program. However only those sequence segments are compared that give a match above a certain threshold. Accordingly, the program calculates the identity only for these matching segments. Therefore, the identity calculated in this way is referred to as local identity.

It will be appreciated that polypeptides described herein can include additional amino acids that are not involved in other enzymatic activities carried out by the enzyme, and thus such a polypeptide can be longer than would otherwise be the case. For example, a polypeptide can include a purification tag (e.g., HIS tag or GST tag), a chloroplast transit peptide, a mitochondrial transit peptide, an amyloplast peptide, signal peptide, or a secretion tag added to the amino or carboxy terminus. In some embodiments, a polypeptide includes an amino acid sequence that functions as a reporter, e.g., a green fluorescent protein or yellow fluorescent protein.

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

As disclosed herein, a "regulatory region" (prokaryotic and eukaryotic) refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof.

A regulatory region typically comprises at least a core (basal) promoter. A regulatory region also can include at least one control element, such as an enhancer sequence, an upstream element, or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region can be present, e.g., introns, enhancers, upstream activation regions, transcription terminators, and inducible elements.

The polypeptides of the invention exhibit at least 20% amino acid sequence identity to any of SEQ ID NOs: 1-3, such as at least 25%, at least 30%, at least 35%, at least 40%, at least 45%, at least 50%, at least 55%, at least 60%, at least 65%, at least 70%, at least 75%, at least 80%, at least 85%, or at least 90% amino acid sequence identity.

In some embodiments, the polypeptides according to any of SEQ ID NOs: 1-3 exhibit at least 81%, 82%, 83%, 84%, 85%, 86%, 87%, 88%, 89%, 91%, 92%, 93%, 94%, 95%, 96%, 97%, 98%, or 99% amino acid sequence identity.

Functional Homologues and Genetic Variation

Functional homologs of the polypeptides described above are also suitable for use in producing the compounds mentioned herein in a recombinant host. A functional homolog is a polypeptide that has sequence similarity to a reference polypeptide, and that carries out one or more of the biochemical or physiological function(s) of the reference polypeptide.

A functional homolog and the reference polypeptide can be natural occurring polypeptides, and the sequence similarity can be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, can themselves be functional homologs. Functional homologs can also be created via site-directed mutagenesis of the coding sequence for a polypeptide, or by combining domains from the coding sequences for different naturally-occurring polypeptides ("domain swapping").

Techniques for modifying genes encoding functional the polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide: polypeptide interactions in a desired manner.

Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of polypeptides described herein.

Typically, polypeptides that exhibit at least about 20% amino acid sequence identity are useful to identify conserved regions. Conserved regions of related polypeptides exhibit at least 25% amino acid sequence identity e.g., at least 30%, at least 40%, at least 55%, at least 50%, at least 60%, at least 70%, at least 80%, or at least 90% amino acid sequence identity. In some aspects the invention relates to a conserved region exhibits at least 92%, 94%, 96%, 98%, or 99% amino acid sequence identity. The conserved region may be considered to be the entire protein or nucleic acid sequence.

An aspect of the invention relates to a functional homologue that has at least 20% sequence identity with an amino acid or nucleic acid sequence mentioned herein, such as 40% sequence identity, such as 50% sequence identity, such as 60% sequence identity, such as 70% sequence identity, such as 75% sequence identity, such as 80% sequence identity, such as 85% sequence identity, such as 90% sequence identity, such as 75% sequence identity, such as 97% sequence identity, such as 98% sequence identity, such as 99% sequence identity.

Method for testing different homologs A person skilled in the art would recognize that beneficial mutations described here can be advantageously applied to sequence homologs from organisms other than *Coptis japonica* resulting in new variants of such homologs with altered properties.

One method to identify the equivalent mutation positions in other homologs would be to align homolog sequences to *Coptis japonica* NCS using a readily available protein alignment tool, and then use the resulting alignment to identify the corresponding position in the homolog at which a mutation is known to be beneficial in the CjNCS sequence SEQ ID NO: 1.

A new homolog variant(s) can then be designed by swapping the wild type amino acid at that position in the homolog with beneficial mutations described herein before synthesizing the new variants and testing for activity in a suitable assay, for example the assay for NCS activity described in this Examples 5, 6 and 7.

For example, a "I178-analog" position corresponds to position I178 according to SEQ ID NO: 1 can be determined by sequence alignment of NCS sequences from organisms other than *Coptis japonica* as explained herein. For example the I178-analog position of NCBI-ProteinID: [AAR22502.1] is position A182, and of NCBI-ProteinID: [ACJ76785.1] the position is S170 and of NCBI-ProteinID: [SEAAX56304.1] is S181.

Corresponding analogies apply to the other sequence positions described for SEQ ID NO: 1 herein, and include A73, I75, A77, and V174 and their analogous positions. The GenBank protein sequence reference number, the amino acid residue "corresponding" to position V174 of SEQ ID NO: 1, i.e. I178-analog ("Aa") and whose sequence position are presented in the Table 1.

For purposes of the invention, in Table 1 below the amino acid sequence SEQ ID NO: 1 was aligned pairwise with the amino acid sequences in Table 1 determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 3.0.0, 5.0.0, 6.6.0 or later. The Needle program of the EMBOSS package creates an optimal global alignment of two sequences using the Needleman-Wunsch algorithm. The parameters used are gap open penalty of 10, gap extension penalty of 0.5, End Gap Penalty is set as false, End Gap Open Penalty of 10.0, End Gap Extension Penalty of 0.5, and the EBLOSUM62 (EMBOSS version of BLOSUM62) substitution matrix Functional homologs can be identified by analysis of nucleotide and polypeptide sequence alignments. For example, nucleic acid that encodes a functionally or polypeptide sequences can identify homologs of polypeptides described herein.

In some embodiments, the coding sequence for a polypeptide described herein is identified in a species other than the recombinant host, i.e., is a heterologous gene.

Thus, if the recombinant host is a microorganism, the coding sequence can be from other prokaryotic or eukaryotic microorganisms, from plants or from animals. In some cases, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant gene construct. In addition, stably transformed exogenous genes typically are integrated corresponding to positions other than the position where the native sequence is found.

One or more genes can be combined in a recombinant nucleic acid construct in "modules" useful for a discrete aspect of production of a compound described herein. Combining a plurality of genes in a module, particularly a polycistronic module, facilitates the use of the module in a variety of species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

TABLE 1

| Organism | GenBank Accession numbers of the Reference sequences | Aa | Position |
|---|---|---|---|
| Coptis japonica | BAF45338.2 | I | 178 |
| Thalictrum flavum | AAR22502.1 | A | 182 |
| Expression vector pWCD2339 | AKH61495.1 | A | 164 |
| Sinopodophyllum hexandrum | AIT42265.1 | A | 175 |
| Argemone mexicana NCS1 | ACJ76785.1 | S | 170 |
| Corydalis saxicola | AEB71889.1 | S | 156 |
| Argemone mexicana NCS2 | ACJ76787.1 | S | 170 |
| Papaver bracteatum | ACO90258.1 | S | 144 |
| Papaver somniferum NCS2 | AAX56304.1 | S | 181 |
| Tinospora cordifolia NCS | AKH61504.1 | G | 142 |
| Papaver bracteatum | ACO90257.2 | S | 313 |
| Papaver somniferum NCS | AKF41585.1 | S | 140 |
| Expression vector pWCD2338 | AKH61498.1 | S | 143 |
| Eschscholzia californica | ACO90254.1 | G | 144 |
| Papaver somniferum | ACI45396.1 | S | 181 |
| Papaver somniferum NCS1 | AAX56303.1 | S | 181 |
| Papaver somniferum | AAX56075.1 | D | 142 |
| Setaria italica | XP_004956360.1 | A | 142 |
| Eschscholzia californica | ACO90255.1 | G | 143 |
| Papaver somniferum | AAX56076.1 | G | 144 |
| Nelumbo nucifera NCS1 | XP_010247383.1 | G | 143 |
| Nelumbo nucifera NCS3 | XP_010274281.1 | G | 142 |
| Nelumbo nucifera NCS4 | XP_010247387.1 | Q | 140 |
| Nelumbo nucifera NCS5 (S-norcoclaurine synthase 2-like) | XP_010247382.1 | E | 142 |
| Nelumbo nucifera NCS7 (S-norcoclaurine synthase 1-like) | AND61512.1 | W | 143 |

Concatemer

A concatemer is a multimeric molecule of DNA formed by multiple Bet v I allergen domains (PF00407) arranged linearly in the same head-to-tail orientation. NCSs have been reported to also occur in 2 or more fused copies.

Based on protein sequence, C. japonica NCS (SEQ ID NO: 1) is classified into the PFAM family Bet v I allergen domains (PF00407).

In case a transcript contains multiple Bet v I allergen domains (PF00407), instead of directly aligning SEQ ID NO: 1 with such a concatemer, one should first identify those domains in the translated sequence with for example PFAM and then align the individual domains and not the complete sequence to SEQ 1.

NCS is a relatively inefficient enzyme as observed by low product formation in heterologous genetically engineered systems and by measuring catalytic activity biochemically. Its catalytic efficiency of $1$ $mM^{-1}s^{-1}$ has been reported to be more that 100-fold lower than the median calculated over all enzymes and the high $K_m$ for dopamine indicates that high substrate concentrations may be required for significant product formation. In Papaveraceae NCS occurs as fusions of two to four repeated domains with confirmed activity. These fusions may constitute a mechanism to increase efficiency of the enzyme.

Thus, the invention also relates to concatemers of the NCS amino acid sequences described herein.

NCS Species Origin

The norcoclaurine synthases from *Thalictrum flavum* is best studied; both biochemical and structural data are available for this enzyme. Low activity is also indicated by the difference in norcoclaurine concentration versus dopamine concentration in yeast strains producing norcoclaurine, being the molar norcoclaurine concentration lower by a factor of up to 100-fold. DeLoache et al, used an NCS from *P. somniferum* (GenBank accession code KP262411), which was selected after screening four NCS variants with homology to a *Thalictrum flavum* NCS (GenBank accession code AC090248.1) for activity in *S. cerevisiae*.

The inventors used a synthase derived from *Coptis japonica*.

Increased Activity

The inventors constructed a protein model of NCS from *Coptis japonica* using the available structural template from *Thalictrum flavum*. Correspondingly, an active site model with accommodated relevant substrates and intermediates was generated.

The model was used to design mutations, which were likely to alter enzymatic activity. Alongside, further techniques which selected mutations based on phylogeny and occurrence were utilized. This led to the identification of mutation sites across the protein which were predicted to increase activity and/or substrate selectivity.

Accordingly, rounds of 30-90 mutations were constructed and a yeast strain was transformed with these constructs. The resulting strains were grown for 72 h in 96-well deep well plates at 30° C. in SC-HIS medium with 0.6 mM ammonium sulfate, 1 mM additional tyrosine and 1.5 mg/ml dopamine.

Samples of the cell culture supernatant were subjected to LC/MS analysis for quantification of norcoclaurine, and under these assay conditions several mutants with increased activity of up to 2-fold compared to wild type were identified (See also FIG. 4).

Thus, in one or more exemplary embodiments, the invention relates to a norcoclaurine synthase having an increased catalysation when compared to the wild type synthase of the condensation of 4-HPAA and dopamine to (S)-norcoclaurine and/or 3,4-DhPAA and dopamine to (S)-norlaudanosoline.

The increased catalysation may manifest in increased product formation of cell cultures after 72 hours cultivation time in the assay conditions described above compared to the norcoclaurine production obtained from a cell comprising SEQ ID NO: 1.

Increased catalytic activity can also be shown in enzymatic assays using a lysate from a bacterial of fungal host adding the substrates 4-HPAA or 3,4-DHPAA in combination with dopamine and measure the formation of the products (S)-norcoclaurine or (S)-norlaudanosoline, respectively. In another assay system the heterologously expressed NCS can be purified from a host and used in an in vitro reaction in a suitable buffer system and with favourable salt concentrations together with the substrates. The product can be measured by a suitable LC/MS method.

Nucleic Acids

In one or more exemplary embodiments, the invention relates to a nucleic acid according to the invention, wherein the nucleic acid sequence is at least 40% identical to the nucleic acid sequence given in SEQ ID No: 2 or SEQ ID No: 4.

As disclosed herein, at least 40% identical to the nucleic acid sequence given in SEQ ID No: 2 or SEQ ID No: 4 relates to at least 45% identical, at least 50% identical, at least 55% identical, at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, at least 99% identical to the nucleic acid sequence given in SEQ ID No: 2 or SEQ ID No: 4.

One or more exemplary embodiments of the invention relates to the nucleic acids described herein encoding the norcoclaurine synthases with the proviso that wild type sequence per se as disclosed in SEQ ID NO: 2 or SEQ ID No: 4 is not included.

When evaluating norcocalurine titers of the cultures after the 72 hours' cultivation time as described herein, the inventors found codon optimized NCS from the flower *Coptis japonica* is the most active enzyme, see FIG. 3.

In one or more exemplary embodiments, the invention relates to a nucleic acid as described above, wherein the nucleic acid is codon optimized for *S. cerevisiae*.

In one or more exemplary embodiments, the codon optimized nucleic acid sequence is at least 80% identical to the nucleic acid sequence given in SEQ ID No: 3 or SEQ ID No: 5, such as 81% identical, 82% identical, 83% identical, 84% identical, 85% identical, 86% identical, 87% identical, 88% identical, 89% identical, 90% identical, 91% identical, 92% identical, 93% identical, 94% identical, 95% identical, 96% identical, 97% identical, 98% identical, 99% identical, or 100 identical to the nucleic acid sequence given in SEQ ID No: 3 or SEQ ID No: 5.

The skilled person would understand that any feature and/or embodiment discussed above in connections with the amino acids according to the invention apply by analogy to the nucleic acids described herein, especially the necessary means for making the site-specific mutations.

The skilled person would understand that the nucleic acids of the invention may be recombinant.

Heterologous Host Cell

At least one of the genes mentioned herein can be a recombinant gene, the particular recombinant gene(s) depending on the species or strain selected for use. Additional genes or biosynthetic modules can be included in order to increase compound yield, improve efficiency with which energy and carbon sources are used to produce the target compounds mentioned herein, and/or to enhance productivity from the cell culture or plant, in a engineered biosynthetic pathway.

The invention also relates to heterologous host cell comprising the nucleic acids described herein. Thus, in one embodiment, the invention relates to a heterologous host cell comprising a nucleic acid according to the invention, wherein the nucleic acid is recombinant.

In some embodiments of the invention, the recombinant host comprises a yeast cell, a plant cell, a mammalian cell, an insect cell, a fungal cell, an algal cell, a cyanobacteria or a bacterial cell.

In some embodiments of the invention, microorganisms can include, but are not limited to, *S. cerevisiae* and *E. coli*. The constructed and genetically engineered microorganisms provided by the invention can be cultivated using conventional fermentation processes, including, inter alia, chemostat, batch, fed-batch cultivations, continuous perfusion fermentation, and continuous perfusion cell culture.

A number of prokaryotes and eukaryotes are suitable for use in constructing the recombinant microorganisms described herein, e.g., gram-negative bacteria, yeast and fungi. A species and strain selected for use as a strain for production of the compounds described herein is first analysed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species can be suitable. For example, suitable species can be in a genus selected from the group consisting of *Agaricus, Aspergillus, Bacillus, Candida, Corynebacterium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* and *Yarrowia*. Exemplary species from such genera include *Lentinus tigrinus, Laetiporus sulphureus, Phanerochaete chrysosporium, Pichia pastoris, Physcomitrella patens, Rhodoturula glutinis* 32, *Rhodoturula mucilaginosa, Phaffia rhodozyma* UBV-AX, *Xanthophyllomyces dendrorhous, Fusarium fujikuroil Gibberella fujikuroi, Candida utilis* and *Yarrowia lipolytics*. In some aspects, a microorganism can be an Ascomycete such as *Gibberella fujikuroi, Kluyveromyces lactis, Schizosaccharomyces pombe, Aspergillus niger*, or *Saccharomyces cerevisiae*.

In some embodiments, a microorganism can be a prokaryote such as *Escherichia coli, Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of the compounds described herein.

Yeast

In some embodiments, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or *Rhodospiridium* sp.

In some embodiments, the yeast cell is a Saccharomycete.

In some embodiments, the yeast cell is a *Saccharomyces cerevisiae* cell.

*Saccharomyces cerevisiae*

*Saccharomyces cerevisiae* is a widely-used organism in synthetic biology and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

The genes described herein can be expressed in yeast using any of a number of known promoters.

In some embodiments, auxotrophic markers for cloning include, but are not limited to, HIS3, URA3, TRP1, LEU2, LYS2, ADE2, and GAL, which allow for selection of recombinant strains with an inserted gene of interest. Auxotrophic markers can be optionally removed from the yeast genome using methods not limited to Cre-Lox recombination or negative selection with 5-fluoroorotic acid (5-FOA). In other aspects, antibiotic resistance, such as kanamycin, can be used as selection marker for construction of recombinant strains.

Algal

In some embodiments, the algal cell is a cell from *Blakeslea trispora, Dunaliella salina, Haematococcus pluvialis, Chlorella* sp., *Undaria pinnatifida, Sargassum, Laminaria japonica, Scenedesmus almeriensis* species.

Cyanobacerial Cell

In some embodiments, the cyanobacerial cell is a cell from *Phormidium laminosum, Microcystis* sp., *Synechococcus* sp., *Pantoea* sp., *Flavobacterium* sp.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Arxula adeninivorans (Blastobotrys adeninivorans)*

*Arxula adeninivorans* is dimorphic yeast (it grows as budding yeast like the baker's yeast up to a temperature of 42° C., above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorgamism.

*Yarrowia lipolytica* can accumulate lipid content to approximately 40% of its dry cell weight and is a model organism for lipid accumulation and remobilization. See e.g., Nicaud, 2012, Yeast 29(10):409-18; Beopoulos et al., 2009, Biochimie 91(6):692-6; Bankar et al., 2009, Appl Microbiol Biotechnol. 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge et al., 2011, Process Biochemistry 46(1):210-8). *Rhodotorula toruloides* strains have been shown to be an efficient fed-batch fermentation system for improved biomass and lipid productivity (Li et al., 2007, Enzyme and Microbial Technology 41:312-7).

*Rhodosporidium toruloides*

*Rhodosporidium toruloides* is oleaginous yeast and useful for engineering lipid-production pathways (See e.g. Zhu et al., 2013, Nature Commun. 3:1 112; Ageitos et al., 2011, Applied Microbiology and Biotechnology 90(4): 1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, Methods Mol Biol. 824:329-58; Khoury et al., 2009, Protein Sci. 18(10):2125-38.

*Hansenula polymorpha (Pichia angusta)*

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, Virol Sin. 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, FEMS Yeast Res. 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et ai, 2014, N Biotechnol. 31 (6):532-7.

*Physcomitrella* spp.

*Physcomitrella* mosses, when grown in suspension culture, have characteristics similar to yeast or other fungal cultures. These genera can be used for producing plant secondary metabolites, which can be difficult to produce in other types of cells.

Methods for the preparation of a (S)-norcoclaurine and/or (S)-norlaudanosoline One further aspect of the invention relates to methods for the preparation of a (S)-norcoclaurine and/or (S)-norlaudanosoline compound. Increased catalytic activity can also be shown in enzymatic assays using a lysate from a bacterial of fungal host adding the substrates 4-HPAA or 3,4-DHPAA in combination with dopamine and measure the formation of the products (S)-norcoclaurine or (S)-norlaudanosoline, respectively.

In another assay system, the heterologously expressed NCS can be purified from a host and used in an in vitro reaction in a suitable buffer system and with favourable salt concentrations together with the substrates. The product can be measured by a suitable LC/MS method.

In one or more exemplary embodiments, the method for the preparation of a (S)-norcoclaurine and/or (S)-norlaudanosoline compound comprise the steps of
  providing a recombinant host cell capable of catalysation of the condensation of 4-HPAA and dopamine to (5)-norcoclaurine and/or 3,4-DhPAA and dopamine to (S)-norlaudanosoline,
  culturing the cells under conditions promoting said catalysation, and optionally
  isolating the (S)-norcoclaurine and/or (S)-norlaudanosoline.

In one or more exemplary embodiments, the invention relates to a method for the preparation of a (S)-norcoclaurine and/or (S)-norlaudanosoline compound, the method comprising the steps of:
  providing recombinant yeast cells, preferably *Saccharomyces cerevisiae* capable of catalysation of the condensation of 4-HPAA and dopamine to (S)-norcoclaurine and/or 3,4-DhPAA and dopamine to (S)-norlaudanosoline,
  culturing the cells under conditions promoting said catalysation, and optionally
  isolating the (S)-norcoclaurine and/or (S)-norlaudanosoline.

In one or more exemplary embodiments, the (S)-norcoclaurine and/or (S)-norlaudanosoline are intermediates in a benzylisoquinoline (BIA) biosynthesis.

One or more exemplary embodiments of the invention relates to a method for the preparation of a (S)-norcoclaurine and/or (S)-norlaudanosoline compound, comprising contacting compound 4-HPAA and dopamine and/or 3,4-DhPAA and dopamine with a recombinant norcoclaurine synthase according to the invention capable of catalysation of the condensation of 4-HPAA and dopamine to (S)-norcoclaurine and/or 3,4-DhPAA and dopamine to (S)-norlaudanosoline.

One or more exemplary embodiments of the invention relates to a method according to method for the preparation of a (S)-norcoclaurine and/or (S)-norlaudanosoline compound as described above, further comprising cultivating a recombinant host cell of the invention in a culture medium in presence of 4-HPAA and dopamine and/or 3,4-DhPAA and dopamine, under conditions in which the one or more recombinant genes encoding the recombinant mutated norcoclaurine synthase(s) according to the invention is/are expressed in presence of 4-HPAA and dopamine and/or 3,4-DhPAA and dopamine.

In one or more exemplary embodiments, said method is performed in vivo.

In one or more exemplary embodiments, said method is performed in vitro.

TABLE 2

Tested Norcoclaurine synthases

| NCS homolog | Protein ID (Uniprot or NCBI) | Nucleotide ID |
|---|---|---|
| *Thalictrum flavum* NCS | AAR22502.1 | AY376412 |
| *Thalictrum flavum* NCS | AAR22502.1 | codon optimized |
| *Thalictrum flavum* NCS GS (Δ1-19) | Based on AAR22502.1 | codon optimized |
| *Thalictrum flavum* NCS (Δ1-19) | Based on AAR22502.1 | codon optimized |
| *Thalictrum flavum* NCS GS | Based on AAR22502.1 | codon optimized |
| *Coptis japonica* NCS | BAF45338.2 | AB267399.2 |
| *Coptis japonica* NCS | BAF45338.2 | codon optimized |
| *Coptis japonica* NCS Long | BAF45337.1 | codon optimized |
| *Nelumbo nucifera* NCS1 | A0A191T7N6 (XP_010247383.1) | codon optimized |
| *Nelumbo nucifera* NCS3 | A0A191T7P4/ XP_010274281.1 | codon optimized |
| *Nelumbo nucifera* 4 | A0A1U7Z8P0/ XP_010247387.1 | codon optimized |
| *Nelumbo nucifera* NCS5 (in database called S-norcoclaurine synthase 2-like) | A0A182C8V5/ XP_010247382.1 | codon optimized |
| *Nelumbo nucifera* NCS7 (in database called S-norcoclaurine synthase 1-like) | A0A182C8V6/ AND61512.1 | codon optimized |
| *Argemone mexicana* NCS1 | ACJ76785.1 | codon optimized |
| *Argemone mexicana* NCS2 | ACJ76787.1 | codon optimized |
| *Papaver somniferum* NCS | AKF41585.1 | codon optimized |
| *Papaver somniferum* NCS1 | AAX56303 | codon optimized |
| *Papaver somniferum* NCS2 | AAX56304.1 | codon optimized |
| *Sinopodophyllum hexandrum* NCS | A0A097H1C2 | codon optimized |
| *Tinospora cordifolia* NCS | AKH61504 | codon optimized |

General

It should be understood that any feature and/or aspect discussed above in connections with the amino acids according to the invention apply by analogy to the nucleotides described herein.

It should be understood that any feature and/or aspect discussed above in connections with the host cells according to the invention apply by analogy to the methods described herein.

All publications, patents and patent applications cited herein are hereby expressly incorporated by reference for all purposes.

Methods well known to those skilled in the art can be used to construct genetic expression constructs and recombinant cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, CA).

A number of terms use herein will be defined below:

As used herein, the singular forms "a", "an", and "the" include plural referents unless the context clearly dictates otherwise. For example, reference to a "nucleic acid" means one or more nucleic acids.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the invention.

As used herein, the terms "polynucleotide", "nucleotide", "oligonucleotide", and "nucleic acid" can be used interchangeably to refer to nucleic acid comprising DNA, RNA, derivatives thereof, or combinations thereof.

As used herein, the terms "microorganism," "microorganism host," "microorganism host cell," "host cell," "recombinant host," "recombinant microorganism host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through stable introduction of one or more recombinant genes.

Generally, introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA. Said recombinant genes are particularly encoded by cDNA.

As used herein, the term "engineered biosynthetic pathway" refers to a biosynthetic pathway that occurs in a recombinant host, as described herein. In some aspects, one or more steps of the biosynthetic pathway do not naturally occur in an unmodified host. In some embodiments, a heterologous version of a gene is introduced into a host that comprises an endogenous version of the gene.

As used herein, the term "endogenous" gene refers to a gene that originates from and is produced or synthesized within a particular organism, tissue, or cell. In some embodiments, the endogenous gene is a yeast transporter. In some embodiments, the transporter is endogenous to S. cerevisiae, including, but not limited to S. cerevisiae strain S288C. In some embodiments, an endogenous yeast transporter gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast transporter gene is deleted. See, e.g., Giaever & Nislow, 2014, Genetics 197 (2):451-65. As used herein, the terms "deletion," "deleted," "knockout," and "knocked out" can be used interchangabley to refer to an endogenous gene that has been manipulated to no longer be expressed in an organism, including, but not limited to, S. cerevisiae. In some embodiments, a deleted/ knocked out gene is a transporter gene or a transcription factor gene that regulates expression of a transporter gene.

As used herein, the terms "heterologous sequence" and "heterologous coding sequence" are used to describe a sequence derived from a species other than the recombinant host or a sequence from the host that has been inserted into the host recombinantly. In some embodiments are wild type sequences inserted to generate and overexpression of the specific gene. The overexpression can come from manipulation of for example the promoter. In some embodiments, the recombinant host is an S. cerevisiae cell, and a heterologous sequence is derived from an organism other than S. cerevisiae. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

As used herein, the terms "variant" and "mutant" are used to describe a protein sequence that has been modified at one or more amino acids, compared to the wild type sequence of a particular protein.

The following figures and examples are provided below to illustrate the invention.

They are intended to be illustrative and are not to be construed as limiting in any way.

NCS catalyzes the condensation of 4-HPAA and dopamine to (S)-norcoclaurine or 3,4-DHPAA and dopamine to (S)-norlaudanosoline.

Figure 1:
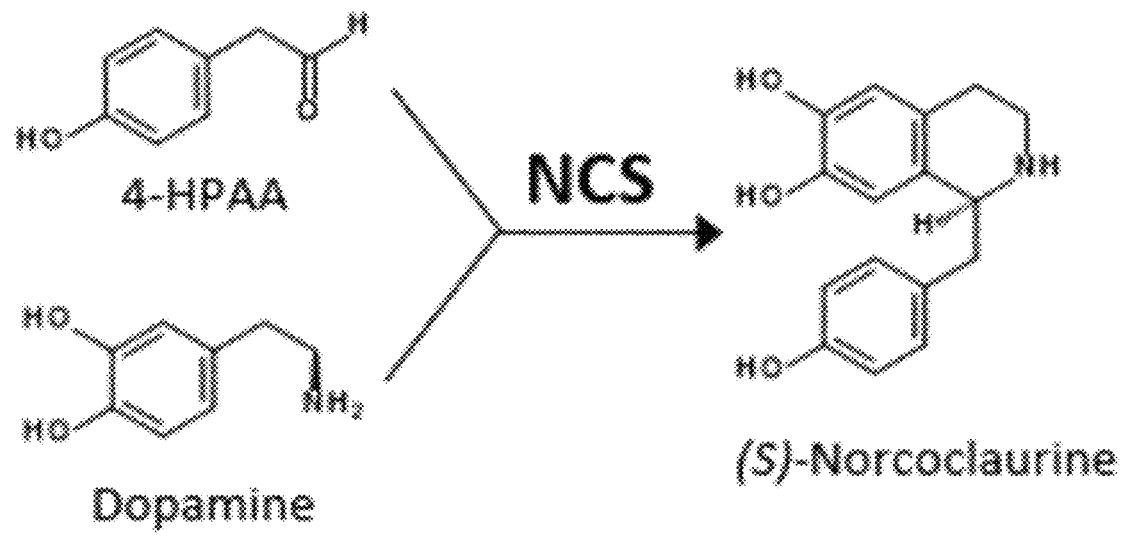
FIG. 1—Condensation
Figure 1:
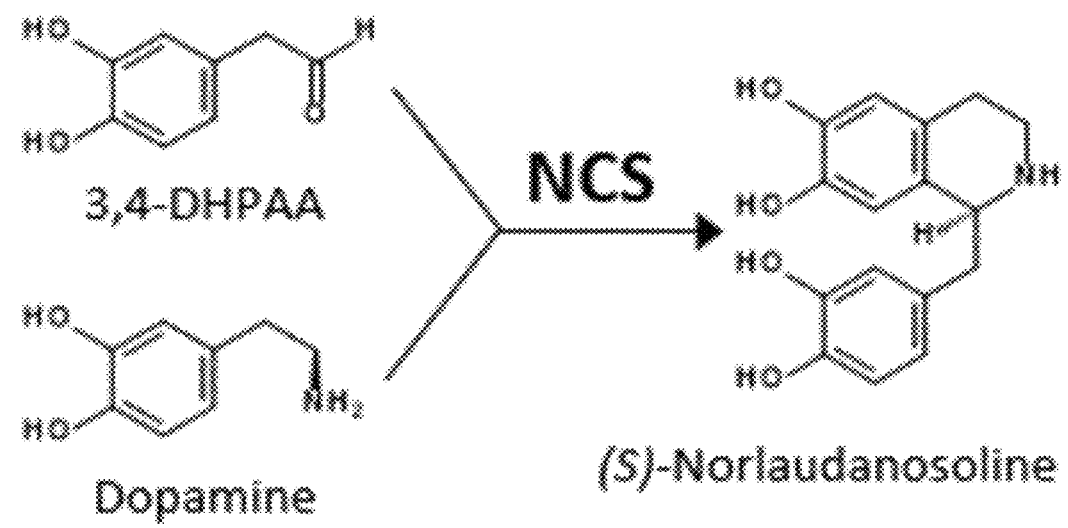
Figure 2:
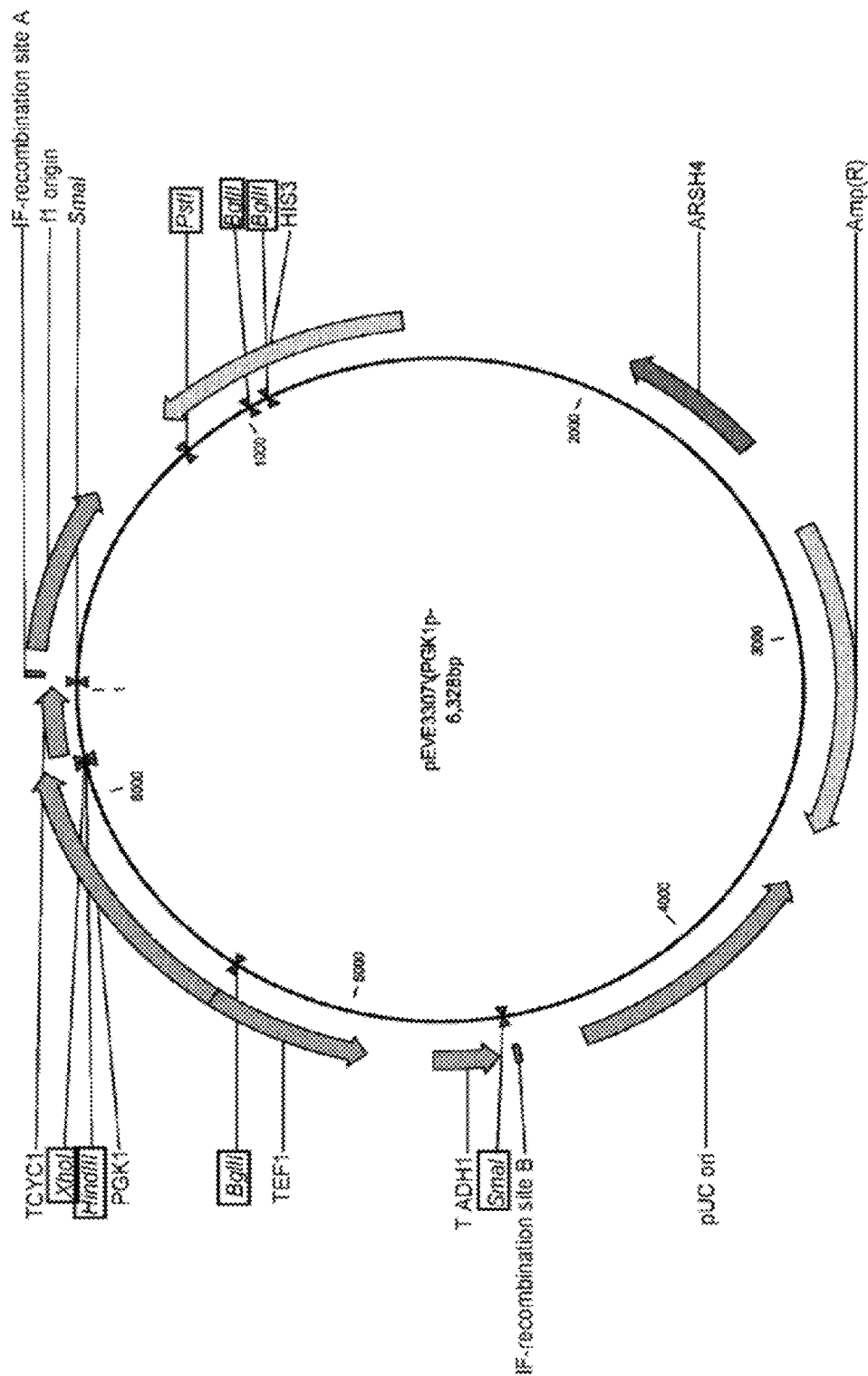

FIG. 2—pEV3307 plasmid

Schematic map of pEV3307 plasmid. Vector elements are annotated.

Figure 3:
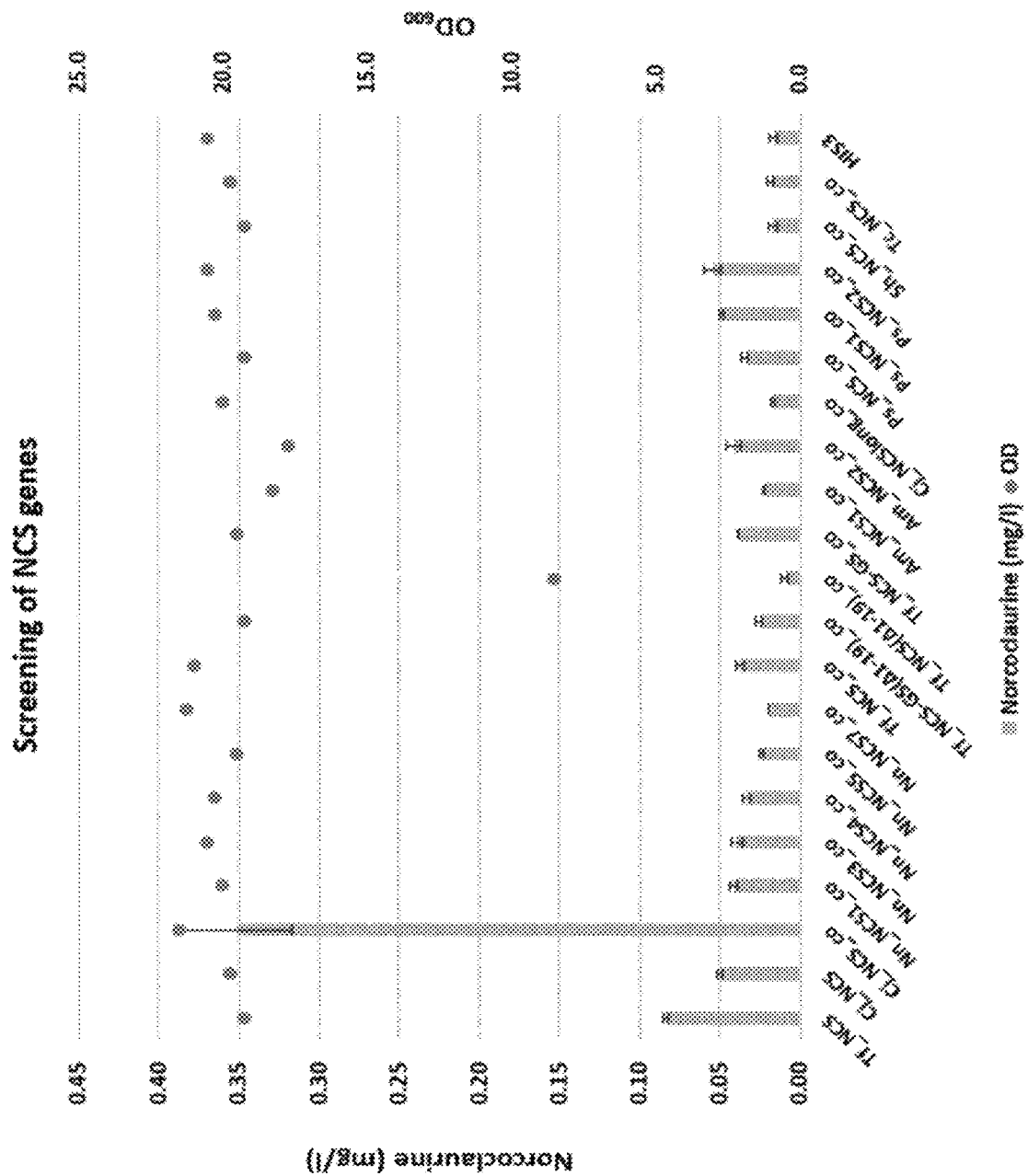

FIG. 3—Norcoclaurine biosynthesis in yeast expressing natural homologs

Screening of NCS homologs from various plant species. Norcoclaurine titers of the cultures after the 72 hours' cultivation time are represented by bars, optical densities of cultures are shown by dots.

Figure 4:
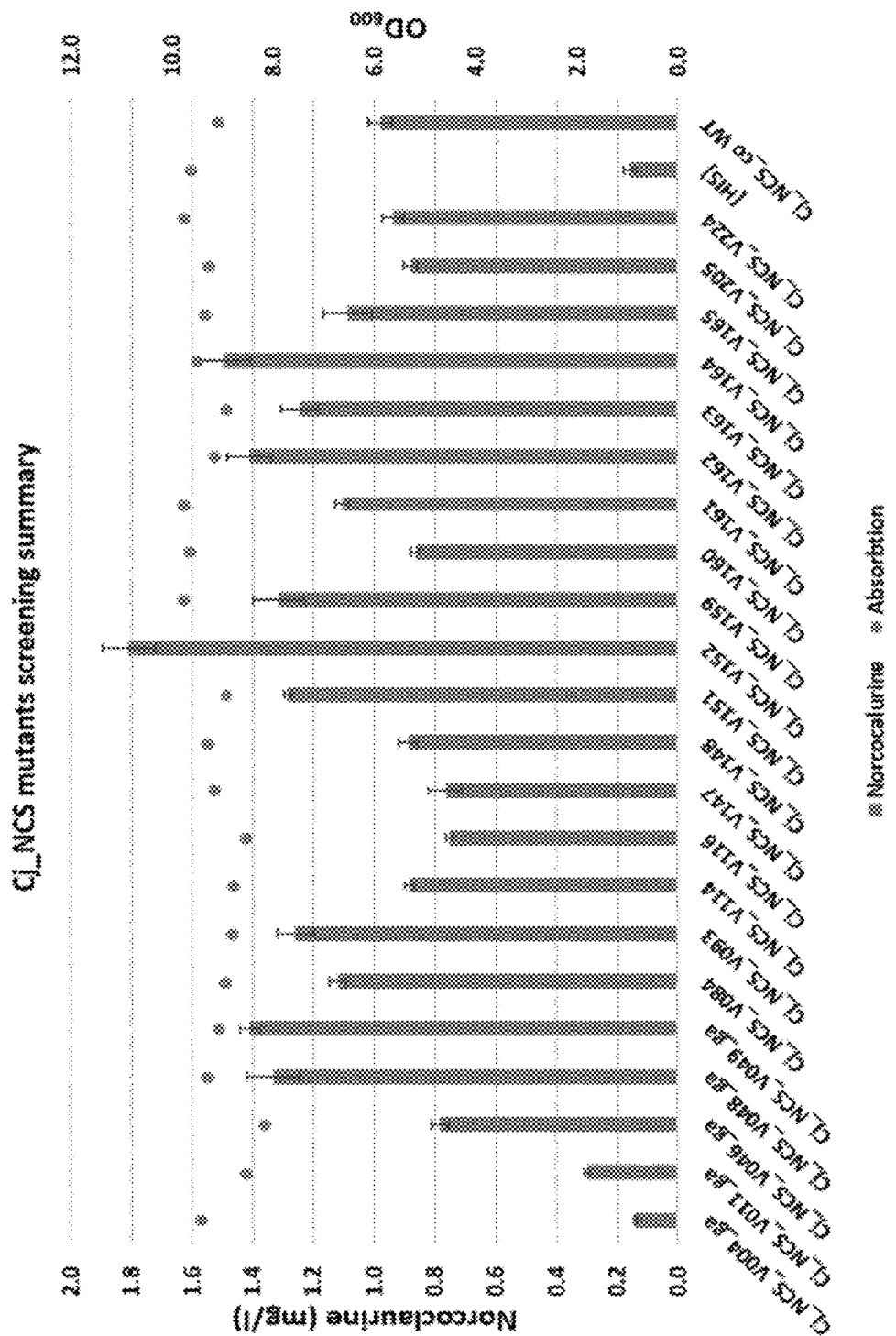

FIG. 4—Norcoclaurine biosynthesis in yeast expressing NCS mutants

Screening of variants of norcoclaurine synthase from *Coptis japonica*. Norcolalurine titers of the cultures after the 72 hours' cultivation time are represented by bars, optical densities of cultures are shown by dots.

Figure 5:
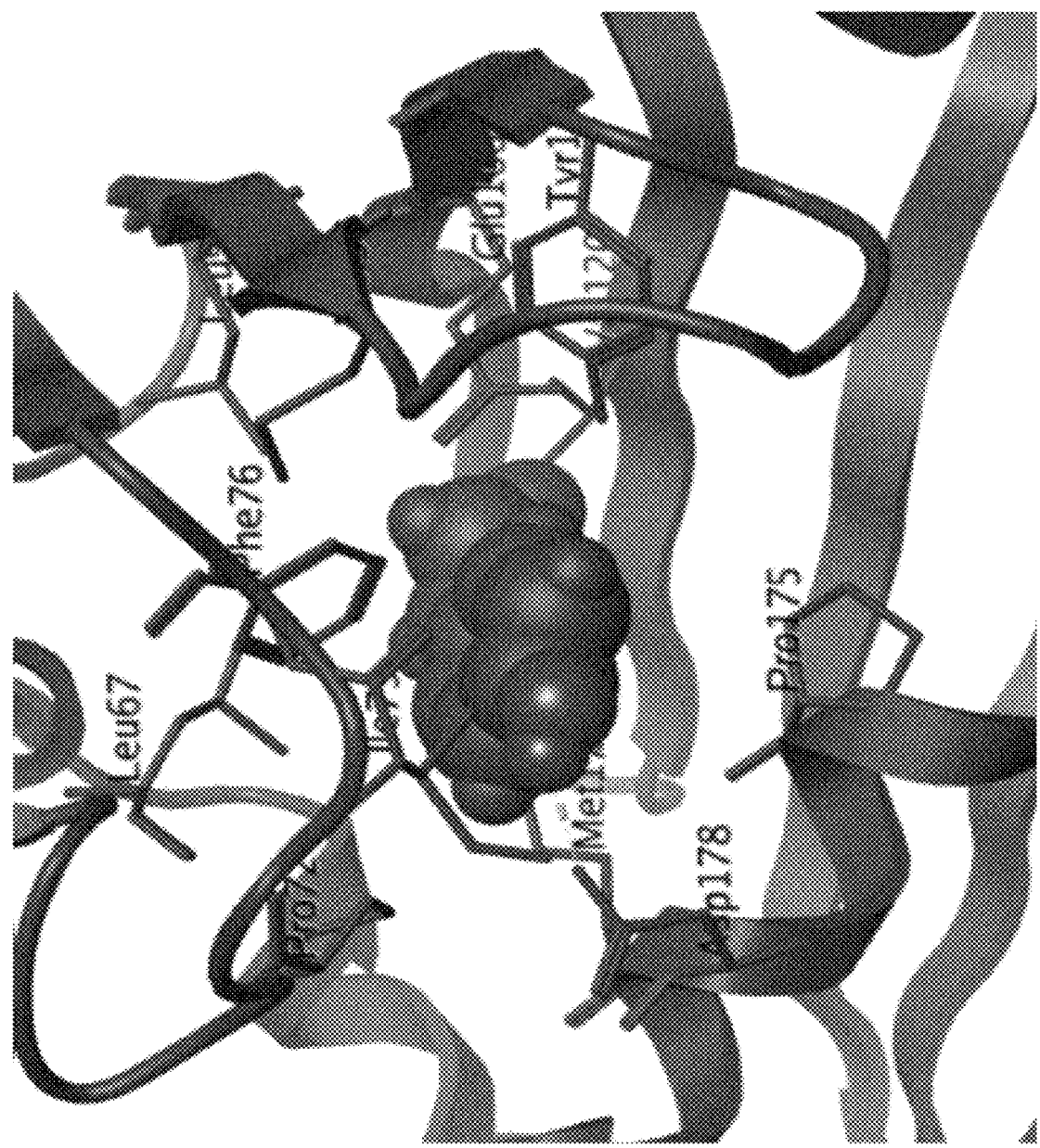

FIG. 5—Cj NCS homology model

Cj NCS homology model with active site predicted residues shown (stick form) and reactive substrates shown in space filling format.

Figure 6:
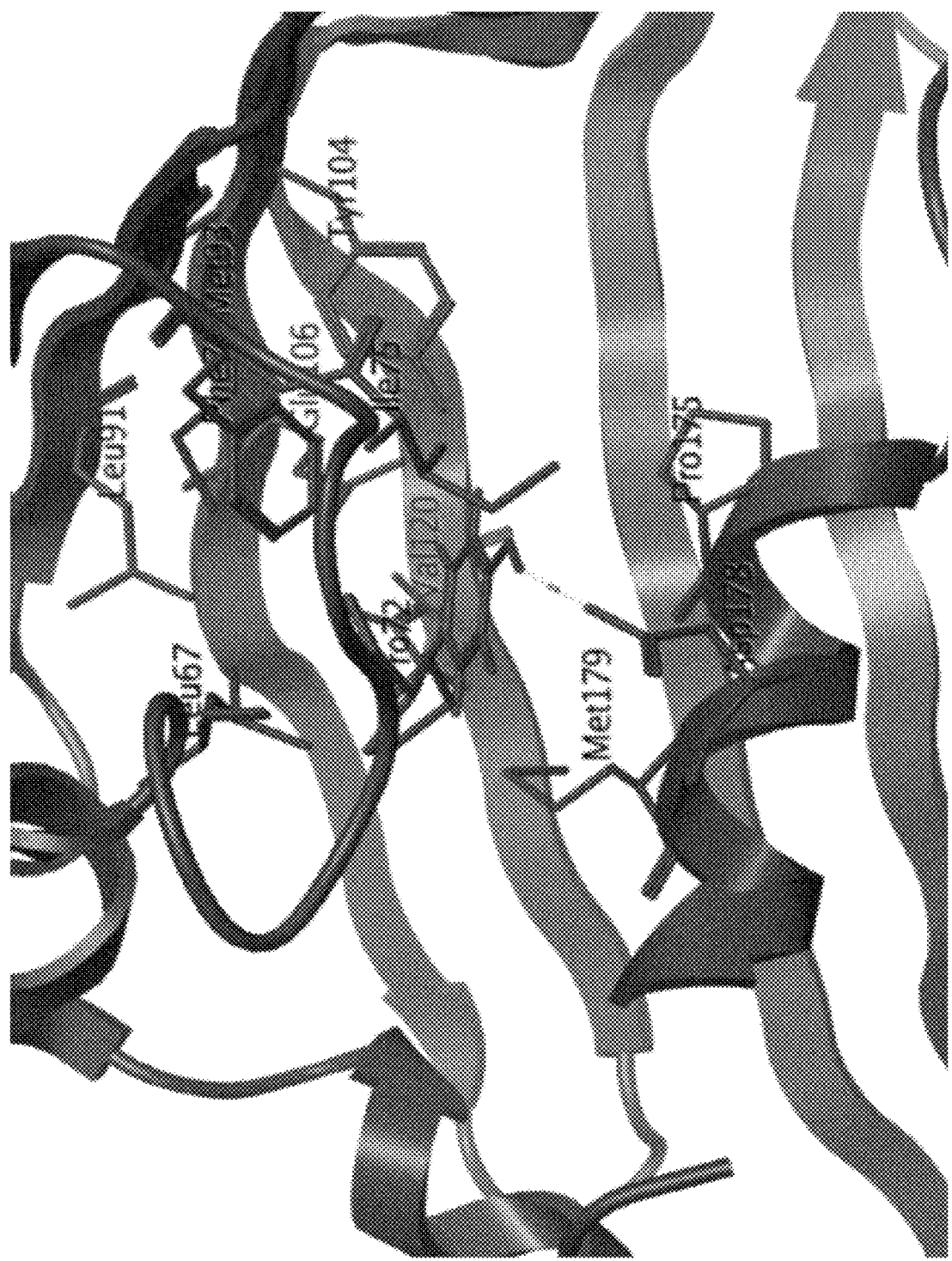

FIG. 6—HPAA substrate enhanced interaction with mutation I178D (magenta)

Modelled interaction between mutant I178D (magenta) and HPAA substrate (cyan). According to this model I178D is predicted to directly interact with aldehyde substrates.

Figure 7:
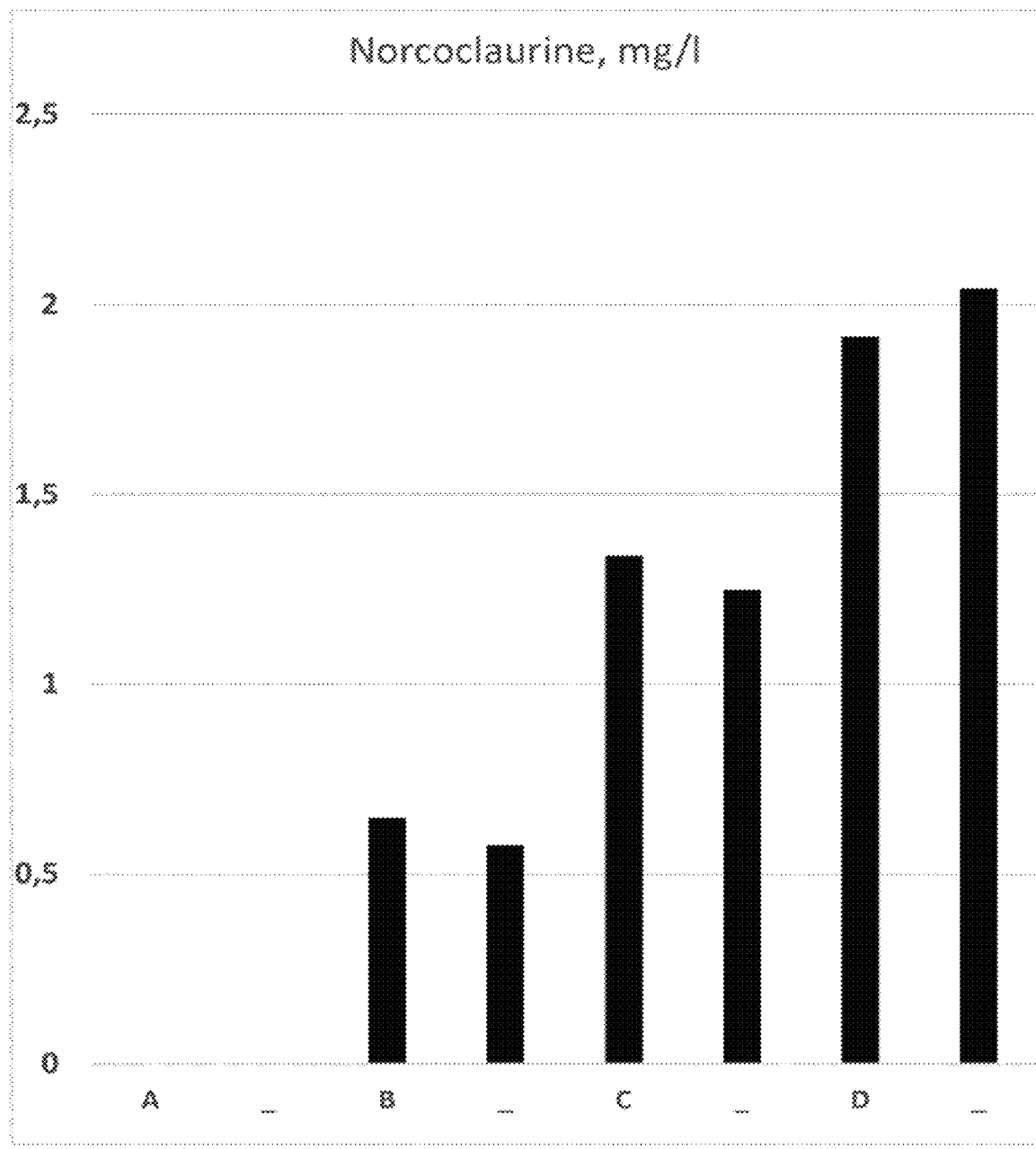

FIG. 7—Disruption of signal peptide function of the *C. japonica* NCS

Figure 8:
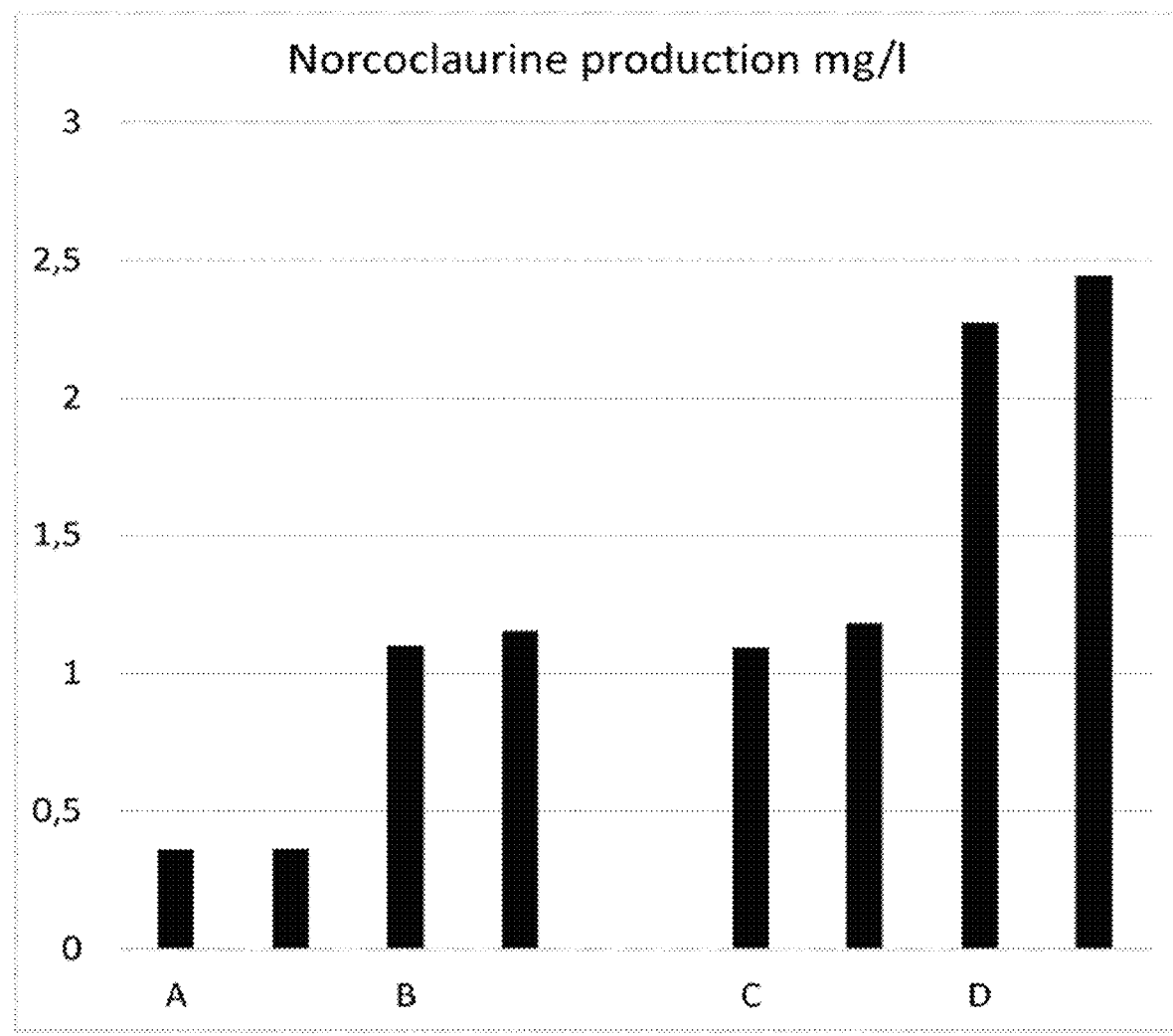

Norcoclaurine production in *S. cerevisiae* increases dramatically when the first 19 amino acids from the N-terminal of the *C. japonica* NCS are replaced by a methionine. Duplicate determinations of norcoclaurine production in 4 different *S. cerevisiae* strains. A) wild type BY4741, B) BY4741 Δari1::ARO4res/PpDODC/CYP76AD1 $^{W13L, F309L}$/CjNCSco, C) BY4741 Δari1::ARO4res/PpDODC/CYP76AD1 $^{W13L, F309L}$/CjNCSco-HDEL, D) BY4741 Δari1::ARO4res/PpDODC/CYP76AD1 $^{W13L, F309L}$/Δ19-CjNCSco FIG. 8—HDEL (SEQ ID NO: 22) addition in the C-terminus The CjNCS I178D improves the activity of the *C. japonica* NCS version with the HDEL (SEQ ID NO: 22) addition in the C-terminus. Duplicate determinations of norcoclaurine production in 4 different *S. cerevisiae* strains. A) Δari1::Aro4$^{FBR}$ CYP76AD1 $^{W13L, F309L}$ PpDODC CjNCS1co. B) Δari1::Aro4$^{FBR}$ CYP76AD1 $^{W13L, F309L}$ PpDODC CjNCS1co$^{I178D}$ C) Δari1::Aro4$^{FBR}$ CYP76AD1 $^{W13L, F309L}$ PpDODC CjNCS1co-HDEL. D) Δari1::Aro4$^{FBR}$ CYP76AD1 $^{W13L, F309L}$ PpDODC CjNCS1co$^{I178D-HDEL}$.

EXAMPLES

Example 1—Protein Model of NCS from *Coptis japonica*—Structural Template

Protein sequences of *Coptis japonica* (Cj) and *Thalictrum flavum* (Tf) NCS were aligned using Clustal Omega (Sievers et al., 2011, Mol Syst Biol. 7:539) along with other NCS homologs identified using the BLASTP algorithm up to 40% identity.

The sequence of Cj NCS has 63% global protein sequence identity to the sequence of *Thalictrum flavum* (Tf) NCS, indicating that their three-dimensional protein structures are highly likely to be similar. Therefore, a protein model of Cj norcoclaurine synthase (NCS) was constructed using the atomic co-ordinates of the protein structure of NCS from *Thalictrum flavum* (Tf) (PDB code 2VQ5; Ilari et al. 2009).

A homology model of Cj NCS was constructed using Homology Model tool in MOE (CCG Inc). A protein modelling software well known and available in the art.

The Cj NCS model allows key residue-specific interactions at the interface between Cj NCS and substrates dopamine and 4-hydroxyphenylacetylaldehyde to be discerned.

Final models were constructed with reactive modelled conformations of dopamine and 4-hydroxyphenylacetylaldehyde [FIG. 5]. These protein models provided the basis to select key residues to mutate in order to affect ligand binding potentials.

Obtained gene sequences were codon optimized for expression in *Saccharomyces cerevisiae*, and their synthesis was performed by Thermofischer Scientific Int. Synthetized genes were cloned in pEV3307 following the procedure described in Example 3. The mutants showing increased NCS versus the wild type enzyme are summarized in Table 8.

Example 2—Cj NCS Activity Increase by Enzyme Engineering Approach—Active Site Model->Design Mutations From the constructed homology model, amino acids were selected for in silico mutation studies using the PROTOSCAN methodology as described by example in WO 2013022881. Briefly, selected amino acids are swapped for each of 19 possible amino acid mutations, the coordinates of which are determined by selection of low energy rotamers before calculating both intra and intermolecular energy of interaction versus wild type residue.

Thus, amino acid mutations can be elucidated, which provide lower binding energy in the context of substrates.

For example, position 178 of NCS contains Isoleucine. PROTOSCAN ranked energies of other mutations at this position and aspartic acid had the lowest energy, because of enhanced interaction with the para hydroxyl group of HPAA substrate as shown in FIG. 6.

The mutation was tested and demonstrated higher activity than the wild type protein. Thus, the in silico screen identified enriching mutation selection versus a random selection of mutants and can effectively sample sequence space in particular, where a substrate binding model is available.

Example 3—Preparation of Expression Vectors

NCS gene sequences from different organisms (Table 2) were identified and codon optimized for expression in *Saccharomyces cerevisiae*.

The synthesis of the resulting sequences was performed by Thermofisher Scientific Inc. Gene sequences and related organism of origin are shown in Table 2.

The newly synthesized genes were cloned in the yeast expression plasmid "pEV3307" (pRS313 modified with the insertion of PGK1 and TEF1 promoters, CYC1 and ADH1 terminators. For basic plasmid details see Mumberg et al. 1995, Yeast vectors for the controlled expression of heterologous proteins in different genetic backgrounds, Gene 156(1):119-22, 1995) carrying the HISS auxotrophic marker.

HindIII/SacII restriction sites were utilized for the insertion of the open reading frames between PGK1 promoter and CYC terminator.

A schematic map of plasmid pEVE3307 with related annotations is shown in FIG. 2.

Example 4—Strain Construction and Expression of NCS Homologs

EVST25898, a modified version of S288C yeast strain (genotype: MATalpha his3Δ0 leu2Δ0 ura3Δ0 aro3Δ::pTEF1-ARO4(K229L)-tCYC1::pPGK1-ARO7(T266L)-tADH1::KI CAT5-91Met GAL2 ho MIP1-661Thr SAL1-1

YORWΔ22::npB101nt-npBIO6nt) was transformed with the constructs described in Example 1.

Yeast transformation was performed according to conventional methods (see R. D. Gietz and R. Woods, "Yeast Transformation by the LiAc/SS Carrier DNA/PEG Method," in Yeast Protocol SE—12, vol. 313, W. Xiao, Ed. Humana Press, 2006, pp. 107-120).

The resulting yeast strains were grown in a 96-deep well plate in appropriate medium (standard SC medium without histidine) for 24h at 30° C. (pre-culture) with 300 rpm shaking. Cells were then inoculated into fresh SC-HIS medium reaching an initial $OD_{600}$~0.1. Obtained cultures were incubated at 30° C. for 72h. After 72h the cells were harvested and the culture supernatants were analyzed according to the methods reported in Examples 6 and 7.

Norcoclaurine was detected in the supernatant of the strain carrying *Coptis japonica* NCS, at a concentration of ~0.35 mg/l. Results are reported in the graph in FIG. 3-4.

Example 5—Screening of Cj_NCS Mutants

Strain EVST25898 was transformed with the constructs obtained in Example 3 (see Example 2 for genotype) in 96 deep well plate format with a commercially available kit (Froze-EZ Yeast transformation II Kit™, Zymo research) according to the manufacturer instructions.

Transformed cells were grown in SC-HIS medium and incubated for 24h at 30° C. under mild shaking. 20 µl of the transformation cultures were used to inoculate a pre-culture in SC-HIS medium (in 96-well format) and the resulting plate was incubated for 24h at 30° C. 5 µl of pre-cultures were inoculated in fresh SC-HIS standard medium, or with modified composition (0.6 mM ammonium sulfate, 1.4 mM tyrosine, 1.5 mg/mg dopamine) and incubated for 72 h.

Analysis of culture supernatants was performed according to the method reported in Examples 6 and 7

A selection of mutants, including the ones showing increased norcoclaurine production versus the control strain after the first screening, were repeated for experimental confirmation and the results of the analysis are shown in FIG. 4.

Variants V48, V49, V93, V151, V152, V240, V241, V242, V246, V247, V249, V253, V261 and V273 showed increased norcoclaurine production up to about 1.8-fold.

Example 6—Norcoclaurine Chiral Analysis

Norcoclaurine HCl (also called higenamine, Carbosynth) solution (1 g/L) was prepared in water. A series of calibration solutions at 4 mg/L, 2 mg/L, 1 mg/L, 0.5 mg/L, 0.25 mg/L, 0.125 mg/L, 62.5 pg/L and 31.25 pg/L in the culture medium was prepared from this stock solution. Caffeine (Sigma) was added to the samples as internal standard to a concentration of 1 mg/L and samples were injected into the UPLC-SQD (Waters).

The LC-MS method was as follows: Mobile Phase A: water+0.1% formic acid; Mobile Phase B: acetonitrile+0.1% formic acid; Column: ORpakCDBS453 (Shodex).

The elution gradient is shown in Table 3 and the LC-MS conditions are given in Table 4.

Table 5 shows the mass spectrometer source and detector parameters. Norcoclaurine and Caffeine were injected analysed in Single Ion Monitoring mode with the respective mass over charge ratio (m/z) 227 and 195 corresponding to their protonated ion. (S)-Norcoclaurine eluted at 5.8 min, (R)-Norcoclaurine at 6.1 min and Caffeine at 6.3 min.

TABLE 3

Gradient for chiral separation

| Time (min) | % B |
| --- | --- |
| 0 | 1 |
| 5 | 35 |
| 8 | 100 |
| 9 | 100 |
| 9.1 | 1 |
| 10 | 1 |

TABLE 4

LC-MS conditions

| | |
| --- | --- |
| Injection volume | 3 µl |
| Column Temperature | 30° C. ± 5° C. |
| Injection method | Partial loop |
| Flow | 0.4 ml/min |
| Auto sampler temperature | 10° C. ± 2° C. |
| Weak wash | 800 µl water/acetonitrile 8:2 |
| Strong wash | 300 µl MeOH |
| Seal wash | 5 min with water/acetonitrile 9:1 |

TABLE 5

Mass spectrometer source and detector parameters (SQD)

| Source Parameter | Value |
| --- | --- |
| Ion Source | Electrospray Positive Mode (ESI+) |
| Capillary Voltage | 3.5 kV |
| Cone Voltage | 20 V |
| Extractor | 3 V |
| RF lens | 0.1 V |
| Source Temperature | 150° C. |
| Desolvation temperature | 350° C. |
| LM resolution | 15 |
| HM resolution | 15 |
| Ion Energy | 0.5 eV |
| Mode | MS |
| LM resolution2 | 15 |
| HM resolution2 | 15 |
| Ion Energy2 | 0.5 |
| API gas | 500 L/hour |

Example 7—Norcoclaurine Non-Chiral Analysis 1 g/L Higenamine HCl (Carbosynth) solution was prepared in water. A series of calibration solutions at 4 mg/L, 2 mg/L, 1 mg/L, 0.5 mg/L, 0.25 mg/L, 0.125 mg/L, 62.5 pg/L and 31.25 pg/L in the culture medium was prepared from this stock solution. Caffeine (Sigma) was added as internal standard to a concentration of 1 mg/L and samples were injected into the UPLC-SQD (Waters).

The LC-MS method was as follows: Mobile Phase A: water+0.1% formic acid; Mobile Phase B: acetonitrile+0.1% formic acid; Column: Aquity BEH C18100×2.1 mm (Waters).

The elution gradient is shown in Table 6 and the LC-MS conditions are given in Table 7.

Table 5 shows the mass spectrometer source and detector parameters. Norcoclaurine and Caffeine were injected analysed in Single Ion Monitoring mode with the respective mass over charge ratio (m/z) 227 and 195 corresponding to their protonated ion. Retention times of Norcoclaurine and Caffeine were 2.5 min and 3.0 min respectively.

TABLE 6

Gradient for non-chiral separation

| Time (min) | % B |
|---|---|
| 0 | 2 |
| 5 | 30 |
| 5.1 | 100 |
| 5.9 | 100 |
| 6 | 2 |
| 8 | 2 |

TABLE 7

LC-MS conditions

| | |
|---|---|
| Injection volume | 5 µl |
| Column Temperature | 30° C. ± 5° C. |
| Injection method | Partial loop |
| Flow | 0.4 ml/min |
| Auto sampler temperature | 10° C. ± 2° C. |
| Weak wash | 800 µl water/acetonitrile 8:2 |
| Strong wash | 300 µl MeOH |
| Seal wash | 5 min with water/acetonitrile 9:1 |

TABLE 8

Mutations with increased activity

| ID | Mutation(s) | Fold increase mutant/WT |
|---|---|---|
| Cj_NCS_V48 | V174G | 1.11 |
| Cj_NCS_V49 | I78A | 1.35 |
| Cj_NCS_V84 | K152R | 1.28 |
| Cj_NCS_V93 | V174E | 1.08 |
| Cj_NCS_V114 | V141I V142I K152R | 1.39 |
| Cj_NCS_V116 | D147N K152R T82V | 1.08 |
| Cj_NCS_V151 | I178S | 1.44 |
| Cj_NCS_V152 | I178D | 2.16 |
| Cj_NCS_V159 | K152R V174E | 1.51 |
| Cj_NCS_V161 | K114E V174E | 1.16 |
| Cj_NCS_V162 | V174G K152R | 1.29 |
| Cj_NCS_V163 | V174G K114E | 1.37 |
| Cj_NCS_V164 | I178A K152R | 1.9 |
| Cj_NCS_V240 | I178N | 1.509 |
| Cj_NCS_V241 | I178Q | 1.767 |
| Cj_NCS_V242 | I178T | 1.111 |
| Cj_NCS_V246 | I178D I75L | 1.469 |
| Cj_NCS_V247 | I178D I75K | 1.859 |
| Cj_NCS_V248 | I178D K152R | 2.002 |
| Cj_NCS_V249 | I178D A77S | 1.567 |
| Cj_NCS_V250 | I178D A77S K152R | 1.761 |
| Cj_NCS_V251 | I178D I75K K152R | 1.77 |
| Cj_NCS_V253 | I178D V174Q | 1.429 |
| Cj_NCS_V258 | I178D V174 K152R | 1.279 |
| Cj_NCS_V261 | A73P A77E | 1.036 |
| Cj_NCS_V263 | I178D K114E K152R | 1.152 |
| Cj_NCS_V267 | I178D V174E Q99K | 1.257 |
| Cj_NCS_V268 | I178D V174Q Q99K | 1.786 |
| Cj_NCS_V269 | I178D V174E Q99R | 1.539 |
| Cj_NCS_V270 | I178D V174Q Q99R | 1.912 |
| Cj_NCS_V271 | I178D V174G K152R A77S | 1.937 |
| Cj_NCS_V273 | A77T I178D | 1.163 |

Example 8—Effect of Norcoclaurine Synthase Localization on Production of Norcoclaurine in *S. cerevisiae*

Based on the *S. cerevisiae* gene integration and expression system developed by Mikkelsen, M D et al (Metab. Eng. 14, Issue 2, 104-111 (2012)), a set of integration/recombination plasmids were designed to simultaneously delete the ORF of the *S. cerevisiae* gene ARI1 and collectively overexpress:

1) a feedback resistant variant of ARO4, ARO4FBR (Luttic, M. A. H et al Metab. Eng.10, 141-153 (2008), 2) a Tyrosine hydroxylase based on the *Beta vulgaris* CYP76AD1 (DeLoache, W. C. et al Nat. Chem. Biol., 11, 465-471 (2015)), 3) the *Pseudomonas putida* DOPA decarboxylase (PpDODC), and 4) several versions of the *Coptis japonica* Norcoclaurine synthase (CjNCS).

All genes used for overexpression were codon optimized for expression in *S. cerevisiae*. The expression cassettes in these integration plasmids were designed to give high expression of the norcoclaurine pathway genes and the following promoters were used: PDC1 promoter (ARO4$^{FBR}$), TDH3 promoter (CYP76AD1$^{W13L, F309L}$), TEF2 promoter (PpDODC), and the PGK1 promoter for expression of the NCS variants.

A laboratory yeast strain (BY4741) transformed with this combined ARI1 deletion/norcoclaurine biosynthesis gene overexpression system gives rise to transformants that show high production of norcoclaurine compared to what was reported in literature (DeLoache, W. C. et al Nat. Chem. Biol., 11, 465-471 (2015)).

Yeast transformants were grown in 96 deep-well plates in 500 µL liquid Synthetic Complete media for 3 days at 30° C. with shaking at 230 rpm in a Kuhner Climo-Shaker ISF1-X. Culture samples for LC-MS were prepared by extraction as follows: 96% ethanol and culture sample were mixed 1:1 and incubated on a heating block at 80° C. for 10 min. After heating cells were pelleted in an Eppendorff table top centrifuge by centrifugation and the supernatant was then transferred to a new tube and diluted 1:5 in water.

Example 9—*Coptis japonica* NCS$^{I178D}$

To test the performance of the NCS$^{I178D}$ version and the NCS$^{I178D}$ with HDEL amino acids added in the C-terminus in this system, new plasmids and yeast strains were constructed.

Again the system described in Example 8 was applied, i.e. deletion of the ORF of ARI1 with simultaneous overexpression of ARO4$^{FBR,}$ CYP76AD1$^{W13L, F309L}$, PpDODC and the various versions of the *C. japonica* NCS.

Example 10—LC-MS Protocol

A Norcoclaurine stock solution was prepared in DMSO at a concentration of 10 mM. Standard solutions were prepared at concentrations of 4 uM, 2 uM, 1 uM, 500 nM, 200 nM, 100 nM, 50 nM and 10 nM from the stock solution. Samples were injected into the Agilent 1290 UPLC coupled to an Ultivo Triple Quadrupole. The LC-MS method was as follows: Mobile Phase A. $H_2O$+0.1% Formic acid; Mobile Phase B: Acetonitrile+0.1% Formic Acid; Column: Phenomenex Kinetex 1.7 um XB-C18 100 Å, 2.1×100 mm. The elution gradient is shown in Table X and the LC-MS conditions are given in Table X. Table X shows the mass spectrometer source and detector parameters and Table X shows the target compound, retention time, parent ion, transition ions (MRM) as well as dwell time, fragmentor voltage and collision energy used.

TABLE 9

Gradient for LC-MS

| Time (min) | % B |
|---|---|
| 0 | 2 |
| 0.30 | 2 |
| 3.00 | 25 |
| 3.40 | 100 |
| 3.90 | 100 |
| 4 | 2 |
| 5 | 2 |

TABLE 10

LC-MS conditions

| Parameter | Value |
|---|---|
| Injection volume | 2 µl |
| Column Temperature | 30° C. ± 4° C. |
| Injection method | Flow through needle |
| Flow | 0.4 ml/min |
| Auto sampler temperature | 10° C. ± 2° C. |
| Reconditioning wash | 2% Acetonitrile (in H$_2$O), 5 sec |
| Weak wash | 20% Methanol (in H$_2$O), 5 sec |
| Strong wash | 30% Acetonitrile, 30% Methanol, 30% 2-Propanol, 10% H$_2$O, 10 sec |
| Seal wash | 20% 2-Propanol (in H$_2$O) |

TABLE 11

Mass spectrometer source and detector parameters (Ultivo Triple Quadrupole)

| Parameter | Value |
|---|---|
| Ion Source | Electrospray Positive Mode (ESI+) |
| Capillary Voltage | 3.5 kV |
| Nozzle Voltage | 500 V |
| Source Gas Temperature | 290° C. |
| Source Gas Flow | 12 L/min |
| Source Sheath Gas Temperature | 380° C. |
| Source Sheath Gas Flow | 12 L/min |
| Nebulizer | 30 psi |
| Mode | MS/MS |
| Collision | See Table 4 |

TABLE 12

Multiple reaction monitoring targets and conditions (ESI+)

| Target compound | Retention time (min) | Parent ion (m/z) | Daughter ion (m/z) | Dwell time (ms) | Fragmentor voltage (V) | Collision energy (V) |
|---|---|---|---|---|---|---|
| Norcoclaurine | 2.29 | 272 | 255 | 200 | 110 | 5 |

REFERENCES

Bonamore, A., Barba, M., Botta, B., Boffi, A. and Macone, A., 2010. Norcoclaurine synthase: mechanism of an enantioselective pictet-spengler catalyzing enzyme. Molecules, 15(4), pp. 2070-2078

DeLoache, W. C. et al. An enzyme-coupled biosensor enables (S)-reticuline production in yeast from glucose. Nat. Chem. Biol. 11,465-471 (2015)

Galanie S, Thodey K, Trenchard I J, Filsinger Interrante M, Smolke C D., 2015. Complete biosynthesis of opioids in yeast. Science. 2015 Sep. 4; 349(6252):1095-100.

Ilari, A., Franceschini, S., Bonamore, A., Arenghi, F., Botta, B., Macone, A., Pasquo, A., Bellucci, L. and Boffi, A., 2009. Structural basis of enzymatic (S)-norcoclaurine biosynthesis. Journal of biological chemistry, 284(2), pp. 897-904

Lichman, B. R., Gershater, M. C., Lamming, E. D., Pesnot, T., Sula, A., Keep, N. H., Hailes, H. C. and Ward, J. M., 2015. 'Dopamine-first'mechanism enables the rational engineering of the norcoclaurine synthase aldehyde activity profile. FEBS journal, 282(6), pp. 1137-1151

Mumberg D, Muller R, Funk M. Yeast vectors for the controlled expression of heterologous proteins in different genetic backgrounds. Gene. 1995; 156:119-122.

Narcross, L., Fossati, E., Bourgeois, L., Dueber, J. E. and Martin, V. J. J. Microbial Factories for the Production of Benzylisoquinoline Alkaloids. Trends Biotechnol. 34, 228-241 (2016)

Mumberg D, Muller R, Funk M. Yeast vectors for the controlled expression of heterologous proteins in different genetic backgrounds. Gene. 156,119-122 (1995)

SEQUENCE LISTING FREE TEXT

SEQ ID NO 1: *Coptis japonica* NCS
SEQ ID NO 2: *Coptis japonica* NCS nucleotide
SEQ ID NO: 3: NCS 2 nucleotide sequence codon optimized for *S. cerevisiae*
SEQ ID NO: 4: *Coptis japonica* NCS wild type loop structure sequence
SEQ ID NO: 5: *Coptis japonica* NCS wild type helix structure sequence
SEQ ID NO: 6: >CYP76AD1 W13L, F309L
SEQ ID NO: 7: >CYP76AD1 W13L, F309L nucleotide sequence codon optimized for *S. cerevisiae*
SEQ ID NO: 8: >PpDODC
SEQ ID NO: 9: >PpDODC nucleotide sequence codon optimized for *S. cerevisiae*
SEQ ID NO: 10: >ARO4$^{FBR}$
SEQ ID NO: 11: >ARO4$^{FBR}$ nucleotide sequence
SEQ ID NO: 12: >CjNCSco
SEQ ID NO: 13: >CjNCSco nucleotide sequence codon optimized for *S. cerevisiae*
SEQ ID NO: 14: >A19-CjNCSco
SEQ ID NO: 15: >A19-CjNCSco nucleotide sequence codon optimized for *S. cerevisiae*
SEQ ID NO: 16: >CjNCSco-HDEL
SEQ ID NO: 17: >CjNCSco-HDEL nucleotide sequence codon optimized for *S. cerevisiae*
SEQ ID NO: 18: >CjNCS1co$^{I178D}$
SEQ ID NO: 19: >CjNCS1co$^{I178D}$ nucleotide sequence codon optimized for *S. cerevisiae*
SEQ ID NO: 20: >CjNCS1co$^{I178D}$-HDEL
SEQ ID NO: 21: >CjNCS1co$^{I178D}$-HDEL nucleotide sequence codon optimized for *S. cerevisiae*

Items of the Invention

1. A norcoclaurine synthase comprising a substrate binding amino acid sequence, which is at least 50% similar to the substrate binding amino acid sequence SEQ ID NO: 4 and/or SEQ ID NO: 5, and wherein the substrate binding amino acid sequence(s) comprise one or more mutations increasing the norcoclaurine synthase activity compared to wild type.

2. A norcoclaurine synthase according to item 1, which has the amino acid Proline (P) corresponding to position 2 in the count according to SEQ ID No. 4.

3. A norcoclaurine synthase according to item 1-2, which has the amino acid Leucine (K) or Lysine (L) corresponding to position 4 in the count according to SEQ ID No. 4.

4. A norcoclaurine synthase according to item 1-3, which has the amino acid Serine (S), Threonine (T) or Glutamic Acid (E) corresponding to position 6 in the count according to SEQ ID No. 4.

5. A norcoclaurine synthase according to item 1-4, which has the amino acid Proline (P) corresponding to position 2 and Leucine (K) or Lysine (L) corresponding to position 4 in the count according to SEQ ID No. 4.

6. A norcoclaurine synthase according to item 1-5, which has the amino acid Proline (P) corresponding to position 2 and Serine (S), Threonine (T) or Glutamic Acid (E) corresponding to position 6 in the count according to SEQ ID No. 4.

7. A norcoclaurine synthase according to item 1-6, which has the amino acid Leucine (K) or Lysine (L) corresponding to position 4 and Serine (S), Threonine (T) or Glutamic Acid (E) corresponding to position 6 in the count according to SEQ ID No. 4.

8. A norcoclaurine synthase according to item 1-7, which has the amino acid Proline (P) corresponding to position 2, Leucine (K) or Lysine (L) corresponding to position 4 and Serine (S), Threonine (T) or Glutamic Acid (E) corresponding to position 6 in the count according to SEQ ID No. 4.

9. A norcoclaurine synthase according to item 1-8 which has the amino acid Glycine (G) or Glutamic Acid (E) corresponding to position 2 in the count according to SEQ ID No. 5.

10. A norcoclaurine synthase according to item 1-9, which has the amino acid Alanine (A), Serine (S) or Aspartic Acid (D) corresponding to position 6 in the count according to SEQ ID No. 5.

11. A norcoclaurine synthase according to item 1-10, which has the amino acid Glycine (G) or Glutamic Acid (E) corresponding to position 2 and Alanine (A), Serine (S) or Aspartic Acid (D) corresponding to position 6 in the count according to SEQ ID No. 5.

12. A norcoclaurine synthase according to any of items 1-11, having an increased catalysation when compared to the wild type synthase of the condensation of 4-HPAA and dopamine to (S)-norcoclaurine and/or 3,4-DhPAA and dopamine to (S)-norlaudanosoline.

13. A norcoclaurine synthase according to any of items 1-12, wherein the increased catalysation manifest in increased norcoclaurine production of cell cultures after 72 hours' cultivation time compared to norcoclaurine production obtained from a cell comprising SEQ ID NO 1 (WILD TYPE).

14. A norcoclaurine synthase according to any of items 1-13, wherein the synthase is derived from *Coptis japonica*.

15. A nucleic acid encoding a norcoclaurine synthase according to any of items 1-14.

16. A nucleic acid according to item 15, wherein the nucleic acid sequence is at least 40% identical to the nucleic acid sequence given in SEQ ID No. 2 (DNA).

17. A nucleic acid according to items 15-16, wherein the nucleic acid is codon optimized for *S. cerevisiae*.

18. A nucleic acid according to items 15-16, wherein the nucleic acid sequence is at least 80% identical to the nucleic acid sequence given in SEQ ID No. 3.

19. A heterologous host cell comprising a nucleic acid according to any one of items 15-18, wherein the nucleic acid is recombinant.

20. The heterologous host cell according to item 19, wherein the cell is a yeast cell, a plant cell, a mammalian cell, an insect cell, a fungal cell, a bacterial cell, an algal cell, or a cyanobacterial cell.

21. The heterologous host cell according to any one of items 19-20, wherein the cell is a yeast cell selected from the group consisting of *Saccharomyces cerevisiae, Schizosaccharomyces pombe, Yarrowia lipolytica, Candida glabrata, Ashbya gossypil, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or *Rhodospiridium* sp.

22. The heterologous host cell according to any one of items 19-21, wherein the host cell is a *Saccharomyces*.

23. The heterologous host cell according to any one of items 19-22, wherein the host cell is a yeast cell is *Saccharomyces cerevisiae* cell.

24. A method for the preparation of a (S)-norcoclaurine and/or (S)-norlaudanosoline compound, the method comprising the steps of:
providing a recombinant host cell according to any of items 19-23, wherein the host cell is capable of catalysation of the condensation of 4-HPAA and dopamine to (S)-norcoclaurine and/or 3,4-DhPAA and dopamine to (S)-norlaudanosoline,
culturing the cell under conditions promoting said catalysation, and optionally
isolating the (S)-norcoclaurine and/or (S)-norlaudanosoline.

25. A method for the preparation of a (S)-norcoclaurine and/or (S)-norlaudanosoline compound, comprising contacting compound 4-HPAA and dopamine and/or 3,4-DhPAA and dopamine with a recombinant norcoclaurine synthase according to any of items 1-14, wherein the recombinant norcoclaurine synthase is capable of catalysation of the condensation of 4-HPAA and dopamine to (S)-norcoclaurine and/or 3,4-DhPAA and dopamine to (S)-norlaudanosoline.

26. The method according to item 25, further comprising cultivating a recombinant host cell of any one of items 19-23 in a culture medium in the presence of 4-HPAA and dopamine and/or 3,4-DhPAA and dopamine, under conditions in which the one or more recombinant genes encoding the recombinant norcoclaurine synthase according to any of items 1-14 is/are expressed in presence of 4-HPAA and dopamine and/or 3,4-DhPAA and dopamine.

27. The method according to item 25-26, which is performed in vitro.

28. A norcoclaurine synthase comprising a substrate binding amino acid sequence, which is at least 20% identical to the substrate binding amino acid sequence SEQ ID NO: 4 and/or SEQ ID NO: 5, and wherein the substrate binding amino acid sequence(s) comprise one or more mutations increasing the norcoclaurine synthase activity compared to wild type.

29. A norcoclaurine synthase according to item 1 or 28, which has the amino acid Proline (P) corresponding to position 2, Leucine (K) or Lysine (L) corresponding to position 4, and/or Serine (S), Threonine (T) or Glutamic Acid (E) corresponding to position 6 in the count according to SEQ ID No: 4.

30. A norcoclaurine synthase according to item 1 or any of 28-29, which has the amino acid Glycine (G) or Glutamic Acid (E) corresponding to position 2, and/or Alanine (A), Serine (S) or Aspartic Acid (D) corresponding to position 6 in the count according to SEQ ID No: 5.

31. A norcoclaurine synthase according to any of items 1 or any of 28-30, having an increased catalysation when compared to the wild type synthase of the condensation of 4-HPAA and dopamine to (S)-norcoclaurine and/or 3,4-DhPAA and dopamine to (S)-norlaudanosoline.

32. A norcoclaurine synthase according to any of items 1 or any of 28-31, which has the amino acid Proline (P) corresponding to position 2 in the count according to SEQ ID No: 4.

33. A norcoclaurine synthase according to item 1 or any of 28-32, which has the amino acid Leucine (K) or Lysine (L) corresponding to position 4 in the count according to SEQ ID No: 4.

34. A norcoclaurine synthase according to item 1 or any of 28-33, which has the amino acid Serine (S), Threonine (T) or Glutamic Acid (E) corresponding to position 6 in the count according to SEQ ID No: 4.

35. A norcoclaurine synthase according to item 1 or any of 28-34, which has the amino acid Proline (P) corresponding to position 2 and Leucine (K) or Lysine (L) corresponding to position 4 in the count according to SEQ ID No: 4.

36. A norcoclaurine synthase according to item 1 or any of 28-35, which has the amino acid Proline (P) corresponding to position 2 and Serine (S), Threonine (T) or Glutamic Acid (E) corresponding to position 6 in the count according to SEQ ID No: 4.

37. A norcoclaurine synthase according to item 1 or any of 28-36, which has the amino acid Leucine (K) or Lysine (L) corresponding to position 4 and Serine (S), Threonine (T) or Glutamic Acid (E) corresponding to position 6 in the count according to SEQ ID No: 4.

38. A norcoclaurine synthase according to item 1 or any of 28-37, which has the amino acid Proline (P) corresponding to position 2, Leucine (K) or Lysine (L) corresponding to position 4 and Serine (S), Threonine (T) or Glutamic Acid (E) corresponding to position 6 in the count according to SEQ ID No: 4.

39. A nucleic acid encoding a norcoclaurine synthase according to any of items 1 or any of 28-38, wherein the nucleic acid sequence is at least 40% identical to the nucleic acid sequence given in SEQ ID No: 4.

40. A heterologous host cell comprising a nucleic acid according to any one of items 1 or any of 28-39, wherein the nucleic acid is recombinant.

41. The heterologous host cell according to item 40, wherein the host cell is a Saccharomyces cerevisiae.

42. A norcoclaurine synthase comprising an amino acid sequence which is at least 40% identical to the amino acid sequence given in SEQ ID No. 1, and which has one or more site-specific mutations corresponding to position 73, 75, 77, 82, 99, 114, 141, 142, 147, 152, 174 and/or 178 of SEQ ID No. 1.

43. A norcoclaurine synthase according to item 42, wherein the site-specific mutation is selected from the group consisting of mutations corresponding A73P, I75L, I75K, A77S, A77E, A77T, T82V, Q99K, Q99R, K114E, V141I, V142I, D147N, K152R, V174E, V174G, V174Q, V174E, I178 Å, I178S, I178D, I178N, I178Q, and I178T of SEQ ID No.

44. A norcoclaurine synthase according to any of items 42-43, having an increased catalysation when compared to the wild type synthase of the condensation of 4-HPAA and dopamine to (S)-norcoclaurine and/or 3,4-DhPAA and dopamine to (S)-norlaudanosoline.

45. A norcoclaurine synthase according to any of items 42-44, wherein the synthase is derived from *Coptis japonica*.

46. A nucleic acid encoding a norcoclaurine synthase according to any of claims items 42-45.

47. A nucleic acid according to claim 46, wherein the nucleic acid sequence is at least 40% identical to the nucleic acid sequence given in SEQ ID No. 2.

48. A nucleic acid according to claims items 46-47, wherein the nucleic acid is codon optimized for *S. cerevisiae*.

49. A nucleic acid according to items 46-47, wherein the nucleic acid sequence is at least 60% identical to the nucleic acid sequence given in SEQ ID No. 3.

50. A heterologous host cell comprising a nucleic acid according to any one of items 46-49, wherein the nucleic acid is recombinant.

51. The heterologous host cell according to item 50, wherein the cell is a yeast cell, a plant cell, a mammalian cell, an insect cell, a fungal cell, a bacterial cell, an algal cell, or a cyanobacterial cell.

52. The heterologous host cell according to any one of items 50-51, wherein the cell is a yeast cell selected from the group consisting of *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinil, Arxula adeninivorans, Xanthophyllomyces dendrorhous, Candida albicans, Rhodotorula* sp., or *Rhodospiridium* sp.

53. The heterologous host cell according to any one of items 50-52, wherein the host cell is a *Saccharomyces*.

54. The heterologous host cell according to any one of items 50-53, wherein the host cell is a yeast cell is a *Saccharomyces cerevisiae* cell.

55. A method for the preparation of a (S)-norcoclaurine and/or (S)-norlaudanosoline compound, the method comprising the steps of:
provproviding a recombinant host cell according to any of items 50-54 capable of catalysing of the condensation of 4-HPAA and dopamine to (S)-norcoclaurine and/or 3,4-DhPAA and dopamine to (S)-norlaudanosoline,
culturing the cell under conditions promoting said catalysation, and optionally
isolating the (S)-norcoclaurine and/or (S)-norlaudanosoline.

56. A method for the preparation of a (S)-norcoclaurine and/or (S)-norlaudanosoline compound, comprising contacting compound 4-HPAA and dopamine and/or 3,4-DhPAA and dopamine with a recombinant norcoclaurine synthase according to any of items 42-49 capable of catalysation of the condensation of 4-HPAA and dopamine to (S)-norcoclaurine and/or 3,4-DhPAA and dopamine to (S)-norlaudanosoline.

57. The method according to item 56, further comprising cultivating a recombinant host cell of any one of items 50-54 in a culture medium in presence of 4-HPAA and dopamine and/or 3,4-DhPAA and dopamine, under conditions in which the one or more recombinant genes encoding the recombinant norcoclaurine synthase according to any of items 42-49 is/are expressed in presence of 4-HPAA and dopamine and/or 3,4-DhPAA and dopamine.

58. The method according to claim 56-57, which is performed in vitro.

59. An opioid selected from the group consisting of Thebaine, Oripavine, Neopinone, Codeinone, Hydrocodone, Morphine, Oxycodone, Codeine, Noscapine, Berberine, Sanguinarine, Tubocurarine and Papaverine obtainable from a method according to any of items 55-58 or 24-27.

The invention claimed is:

1. A variant norcoclaurine synthase comprising an amino acid sequence which is at least 80% identical to the amino acid sequence of SEQ ID NO: 1, and which has one or more site-specific substitution corresponding to position 73, 77, 99, 114, 142, 152, 174 and/or 178 of SEQ ID NO: 1.

2. The variant norcoclaurine synthase according to claim 1, wherein the one or more site-specific substitution is one or more of A73P, A77S, A77E, A77T, Q99K, Q99R, K114E, V142I, K152R, V174E, V174G, V174Q, V174E, I178A, I178S, I178D, I178N, 1178Q, and I178T of SEQ ID NO: 1.

3. The variant norcoclaurine synthase according to claim 1, wherein the variant norcoclaurine synthase comprises the amino acid sequence HDEL (SEQ ID NO: 22) at the C-terminus of the variant norcoclaurine synthase.

4. The variant norcoclaurine synthase according to claim 1 further comprising a non-functional signal peptide.

5. The variant norcoclaurine synthase according to claim 1, having an increased catalysation of the condensation of 4-hydroxy-phenylacetaldehyde (4-HPAA) and dopamine to (S)-norcoclaurine and/or 3,4-dihydroxy-acetaldehyde (3,4-DhPAA) and dopamine to (S)-norlaudanosoline when compared to a wild-type synthase of SEQ ID NO: 1.

6. The variant norcoclaurine synthase according to claim 1, comprising site-specific substitutions at positions 141/142/152, 75/178, or 75/152/178 of SEQ ID NO: 1.

7. The variant norcoclaurine synthase according to claim 6, wherein the site-specific substitutions are V141I/V142I/K152R, I75L/1178D, I75K/1178D, or I75K/K152R/1178D, of SEQ ID NO: 1.

8. A nucleic acid encoding a norcoclaurine synthase according to claim 1.

9. The nucleic acid according to claim 8, wherein the nucleic acid sequence is at least 70% identical to the nucleic acid sequence of SEQ ID NO: 2.

10. The nucleic acid according to claim 8, wherein the nucleic acid is codon optimized for *S. cerevisiae*.

11. The nucleic acid according to claim 8, wherein the nucleic acid sequence is at least 60% identical to the nucleic acid sequence of SEQ ID NO: 3.

12. The nucleic acid according to claim 8, wherein the nucleic acid sequence is at least 80% identical to the nucleic acid sequence of SEQ ID NO: 3.

13. A heterologous host cell comprising the variant norcoclaurine synthase according to claim 1, wherein the norcoclaurine synthase is heterologous to the host cell.

14. The heterologous host cell according to claim 13, wherein the cell is a yeast cell, a plant cell, a mammalian cell, an insect cell, a fungal cell, a bacterial cell, an algal cell, or a cyanobacterial cell.

15. The heterologous host cell according to claim 13, wherein the cell is a yeast cell selected from the group consisting of *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous, Candida albicans, Rhodotorula* sp., or *Rhodospiridium* sp.

16. The heterologous host cell according to claim 13, wherein the host cell is a *Saccharomyces*.

17. The heterologous host cell according to claim 13, wherein the host cell is a yeast cell is a *Saccharomyces cerevisiae* cell.

18. A method for preparing a (S)-norcoclaurine and/or (S)-norlaudanosoline compound, the method comprising the steps of:
providing a recombinant host cell according to claim 13, capable of catalysing the condensation of 4-hydroxy-phenylacetaldehyde (4-HPAA) and dopamine to (S)-norcoclaurine and/or 3,4-dihydroxy-acetaldehyde (3,4-DhPAA) and dopamine to (S)-norlaudanosoline, and
culturing the cell under conditions promoting said catalysation; and optionally isolating the (S)-norcoclaurine and/or (S)-norlaudanosoline.

* * * * *